US010207070B2

(12) United States Patent
Bayer et al.

(10) Patent No.: US 10,207,070 B2
(45) Date of Patent: Feb. 19, 2019

(54) SEAL FORMING PORTION, PAD AND CUSHION FOR A PATIENT INTERFACE AND METHOD OF MANUFACTURING

(71) Applicant: ResMed Limited, Bella Vista NSW (AU)

(72) Inventors: Christian Bayer, Penzberg (DE); Achim Biener, Aufkirchen (DE); Johann Sebastian Burz, Germaringen (DE); Robert Eibl, Bad Toelz (DE); Andreas Kirchberger, Miesbach (DE); Bernd Christoph Lang, Graefelfing (DE); Johannes Nickol, Neukenroth (DE); Jens Rothfuss, Munich (DE)

(73) Assignee: ResMed Limited, Bella Vista (AU)

( * ) Notice: Subject to any disclaimer, the term of this patent is extended or adjusted under 35 U.S.C. 154(b) by 897 days.

(21) Appl. No.: 14/741,930

(22) Filed: Jun. 17, 2015

(65) Prior Publication Data

US 2016/0001029 A1 Jan. 7, 2016

(30) Foreign Application Priority Data

Jun. 17, 2014 (EP) .................................... 14172818

(51) Int. Cl.
*A61M 16/06* (2006.01)
(52) U.S. Cl.
CPC ..... *A61M 16/0611* (2014.02); *A61M 16/0638* (2014.02); *A61M 2016/0661* (2013.01); *A61M 2205/0222* (2013.01)
(58) Field of Classification Search
CPC .......... A61M 16/0611; A61M 16/0638; A61M 2016/0661; A61M 2205/0222; A61M 16/0616; A61M 16/0627; A61M 16/0833
See application file for complete search history.

(56) References Cited

U.S. PATENT DOCUMENTS

| 2005/0022820 A1* | 2/2005 | Kwok ................... | A61M 16/06 128/206.21 |
| 2005/0199239 A1 | 9/2005 | Lang et al. | |
| 2008/0053450 A1* | 3/2008 | Van Kerkwyk ....... | A61M 16/06 128/206.24 |

FOREIGN PATENT DOCUMENTS

| EP | 2 269 679 | 1/2011 |
| WO | WO 2006/074513 | 7/2006 |

(Continued)

OTHER PUBLICATIONS

Communication Pursuant to Article 94(3) EPC dated Jan. 16, 2017 in European Application No. 14 172 818.8 (4 pages).

(Continued)

*Primary Examiner* — Gregory Anderson
*Assistant Examiner* — Jonathan Paciorek
(74) *Attorney, Agent, or Firm* — Nixon & Vanderhye P.C.

(57) ABSTRACT

It is discloses a patient interface 3000 comprising a seal forming portion 11, a pad 10, and a cushion 20. The seal forming portion 11 may comprise a base surface 111 and a plurality of fibers 112 fixed to and extending away from said base surface 111 for contacting a patient's skin. The cushion 20 may comprise at least along a portion of the circumference a first structure 22 having an elongate section 24 joined with at least one end section 26 oriented substantially perpendicular or at an angle to the elongate section 24. A first end A of the elongate section 24 may be connected or connectable to a frame member 30. The end section 26 may be provided at an opposing second end B of the elongate section 24. The pad 10 may comprise a resilient foam material layer with the seal forming portion 11. The pad 10 may be adapted to be connected to the cushion 20.

14 Claims, 15 Drawing Sheets

(56) References Cited

FOREIGN PATENT DOCUMENTS

| WO | WO 2012/058322 | 5/2012 |
| WO | WO 2013/001489 | 1/2013 |
| WO | WO 2013/064950 | 5/2013 |
| WO | WO 2013/144753 | 10/2013 |

OTHER PUBLICATIONS

Search Report for NZ 626663, dated Sep. 4, 2014, 3 pages.
Search Report for EP 14 17 2818, dated Jan. 9, 2015, 13 pages.

\* cited by examiner

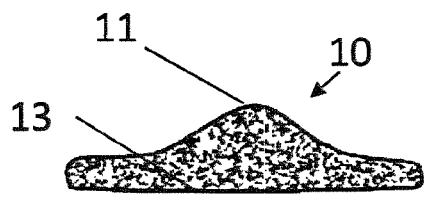
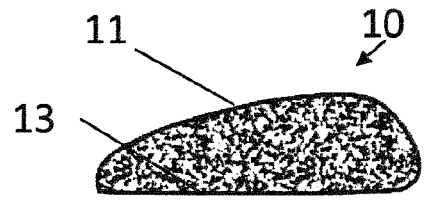
Fig. 8a  Fig. 8b
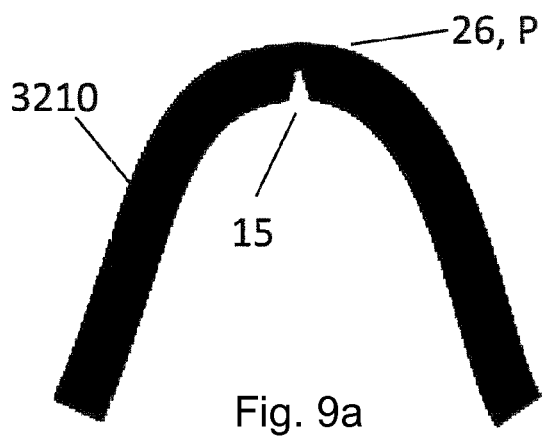
Fig. 9a
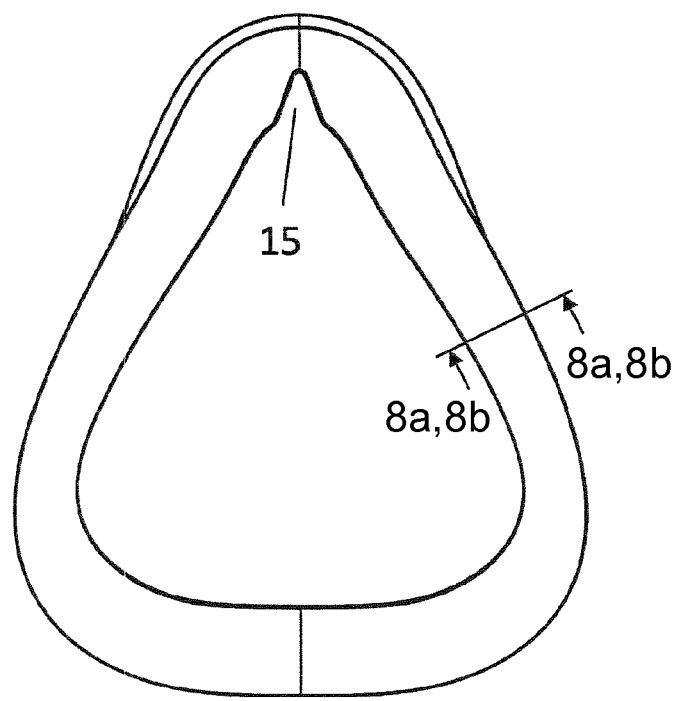
Fig. 9b

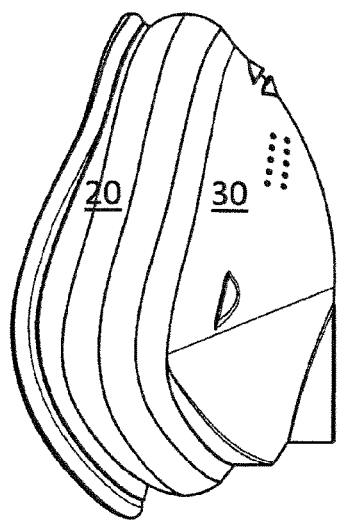
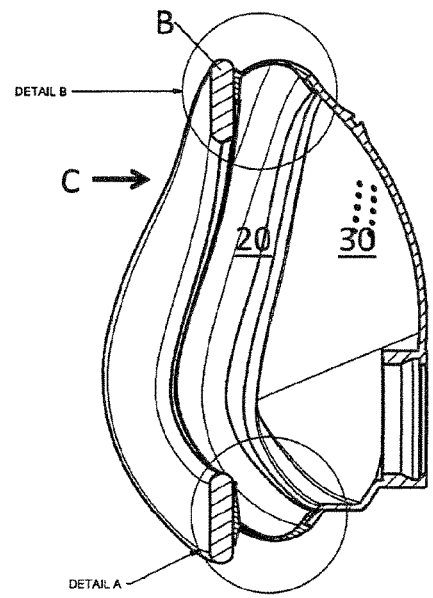
Fig. 11a       Fig. 11b
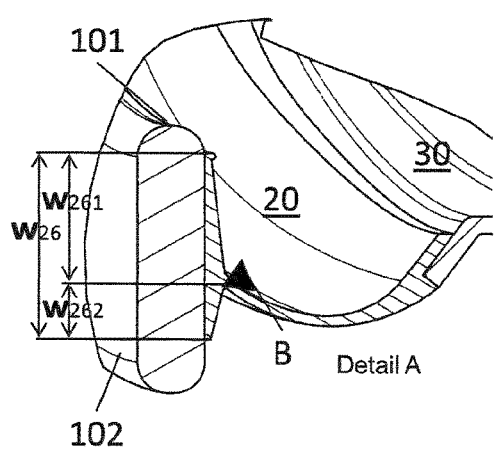
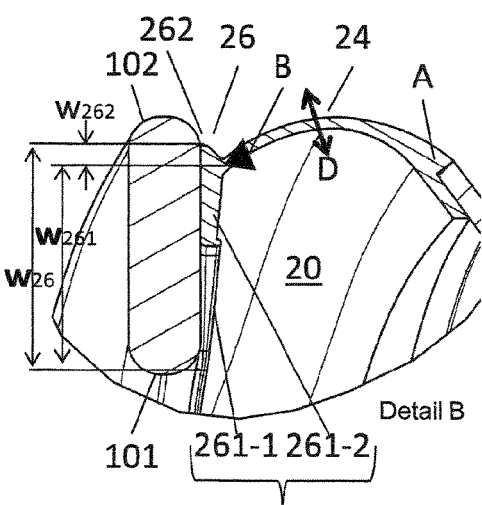
Fig. 11c       Fig. 11d

SEAL FORMING PORTION, PAD AND CUSHION FOR A PATIENT INTERFACE AND METHOD OF MANUFACTURING

CROSS REFERENCE TO RELATED APPLICATION

This application claims priority to EP Patent Application No. 14 17 2818.8 filed 17 Jun. 2014, the entire contents of which is hereby incorporated by reference.

BACKGROUND OF THE INVENTION (1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal forming portion incorporates a cushion with a plastic deformation element, which is adapted to be deformed by the user. The plastic deformation element is adapted to keep the cushion in a deformed shape. The elastic deformation of a cushion with a plastic deformation element tends to be limited and unintentional deformation may occur. Moreover, a releasable seal applied to a patient interface is known.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074.513; WO 2010/135,785.

Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

PAP Device

The air at positive pressure is typically supplied to the airway of a patient by a PAP device such as a motor-driven blower. The outlet of the blower is connected via a flexible delivery conduit to a patient interface as described above.

BRIEF SUMMARY OF THE TECHNOLOGY

The present technology is directed towards providing medical devices used in the amelioration, treatment, or prevention of respiratory disorders having one or more of improved comfort, cost, efficacy, ease of use and manufacturability.

A first aspect of the present technology relates to apparatus used in the amelioration, treatment or prevention of a respiratory disorder.

It is an object of the present invention to overcome or ameliorate the aforementioned drawbacks of the prior art and to provide an improved and/or alternative and/or additional seal forming portion, pad and cushion for a patient interface and a method of manufacturing.

One form of the present technology comprises a seal forming portion for a patient interface. The seal forming portion contacts a user's skin. The patient interface is for providing a respiratory gas to a user, which is preferably delivered via a hose or tube by a system for treating sleep disordered breathing to the patient interface and thus to the patient. The seal forming portion may comprise a base surface, preferably facing a patient's face during use, and a plurality of fibers, filaments and/or threads, preferably attached to said base surface and, preferably, facing a patient's face during use. The plurality of fibers, filaments and/or threads is hereafter described as a plurality of fibers. The plurality of fibers may extend away from said base surface. Preferably, the plurality of fibers is fixed to said base surface. The fibers may extend away from said base surface for contacting, preferably sealingly, a user's skin.

The seal forming portion may provide an improved tactile experience and may be more pleasant to wear. The user may more likely and more often use the patient interface and/or may be able to wear it for extended time periods without experiencing adverse effects such as redness, pressure sores etc. The seal forming portion having a plurality of fibers extending away from said base surface and contacting a user's skin may allow for improved sweat dissipation through the fibers. The seal forming portion may improve the ventilation of the contact surface. The fibers may create a kind of slight, diffused leakage, preferably across the entire sealing surface. This diffused leakage may be perceived by users as a cooling, pleasant feeling, as opposed to a localized, punctual leakage often present in common patient interfaces using membranes, which is perceived as disturbing. Furthermore, the fiber length of the plurality of fibers may, in combination and in balance with the width of the contact surface and the sealing force applied by the sealing pad's preferred features to be later discussed herein, such as a T- or I-beam structure, be specified such that a slight and diffused pleasant, cooling leakage perception is promoted, without drifting off into a too large leak rate which may otherwise be perceived as a poor seal. Moreover, the seal forming portion may improve the self-positioning of the patient interface, preferably in the nose region. This may be achieved, e.g., by a particular and preferred orientation of the fibers and/or by the lower coefficient of friction between fibers and the patient's skin, particularly compared to traditional silicone membranes. Silicone membranes, for instance, may have a tendency to adhere to the skin, so the user effectively has to lift the cushion off the skin and re-position it. Fibers may have a much lower tendency to adhere to the user's skin; therefore the mask cushion may be repositioned without removing it from the face, even during therapy.

Preferably, the plurality of fibers extends in the application position from the base surface towards the user's skin. The plurality of fibers may comprise a proximate end fixed to the base surface and a free distal end preferably adapted to be in contact with a user. Preferably, the plurality of fibers extends at an angle α of about 60°-120°, more preferably of about 75°-105°, and most preferably of about 90° from the base surface (in cases of doubt, preferably, from the tangent to the base surface). In other configurations the preferred angle may be about 45°. These angles refer to the unworn or unused state of the cushion while it will be understood that the orientation of the fibers may change when contacting or being pressed against a user's face. The plurality of fibers may be arranged substantially parallel to each other. The orientation of the plurality of fibers may also change in different regions of the interface or base surface. Alternatively or additionally, the fibers may be arranged at a density between about 10 to 100 g/m$^2$, preferably between about 20 and 65 g/m$^2$, and most preferably between about 30 and 45 g/m$^2$. The fibers may also be randomly oriented. Fibers may be made of viscose and/or polyamide. Viscose fibers may be arranged between about 10 and 50 g/m$^2$, more preferably between about 20 and 40 g/m$^2$, and most preferably between about 25 and 35 g/m$^2$. Polyamide fibers may be arranged at a density between about 25 and 65 g/m$^2$, more preferably between about 35 and 55 g/m$^2$, and most preferably between about 40 and 50 g/m$^2$. Alternatively or additionally, preferably, the fiber(s) has/have a length or height measured from the proximate end to the distal end of between about 0.01 and 5.0mm, more preferably between about 0.05 and 2.0mm and most preferably between about 0.1 and 1.0mm. The fiber(s) may have a substantially round cross sectional shape. Alternatively or additionally, the fiber(s) may have a titre (yarn count) value [dtex] in a range of about 0.01 to 10 dtex, more preferably about 0.1 to 5 dtex, most preferably of about 0.5 to 2 dtex, wherein the Dtex is measured in g/10.000 m. The fiber(s) may be adapted to collapse, preferably in the application position and thus, when being pressed against a user's face. Preferably, the fibers simply bend away or buckle, rather than be compressed. The fiber(s) may predominantly tilt and/or bulge.

The fiber(s) may provide an adapted or controllable softness or resilience. Moreover, the sealing and/or ventilation as well as the sliding resistance may be adaptable/controllable by the variation of the above parameters of the fiber(s). By selecting the length, density, diameter, material and/or arrangement of the fiber(s), such as the orientation of the fiber(s), the properties of the seal forming portion may be adapted to a particular need. For instance, an open cell foam material may be provided with a seal forming portion providing airtight properties to the open cell foam which may reduce the risk of unintended leakage. The seal forming portion may be of a seal forming structure. The seal forming portion may form a perimeter arranged to surround an entrance to the airways of the patient so as to facilitate the supply of air at positive pressure to the airways. The patient interface preferably sealingly contacts a user's face. However a defined, diffused leakage at the seal forming portion located around the entire perimeter may amount to between 2 l/min and 60 l/min, preferably between about 5 l/min to 30 l/min.

The seal forming portion may form an opening for receiving a patient's nose and/or mouth. Preferably, it forms at least a portion of and preferably the whole perimeter of such an opening. The seal forming portion is preferably essentially triangularly shaped. The seal forming portion may contact the user's face around nose ridge (nasal bone, lateral cartilage, septum cartilage) and the lip superior or lip inferior. The seal forming portion may have other alternative configurations such as a nasal pillow configuration with a shape adapted to cover the nostrils.

The fibers may have a varying resilience along the perimeter of the seal forming portion. In particular, the fibers may provide in the application position a higher resilience in the nose bridge area than in other areas of the seal forming portion.

The fibers may be affixed to the base surface by an adhesive. Any suitable bio-compatible adhesive may be used. For instance, the adhesive may be coated on the base surface. Alternatively or additionally, the base surface material itself may be adapted to hold or fix the fibers. The seal forming portion may be made of or may comprise a resilient material, preferably adaptable to the contour of a user's face. For instance the resilient material may provide the base surface. In this configuration not only the fibers but also the material of the seal forming portion improves the adaptability of the patient interface since not only the fibers provide resilience but also the material of the portion to which the fibers are fixed.

The seal forming portion may be made of or comprise a foamed or foam material. The foamed material may provide an additional resilience. As outlined above, air tightness of the seal forming portion may be improved by applying the seal forming portion on open cell foam. The seal forming portion may be made of or comprise a textile material, preferably a resilient textile. Besides foam and textile materials also other bio compatible materials may be used as the base material of the surface to which the fibers are fixed as long as the material provides appropriate mechanical properties comparable to those of a foam or textile material and as long as the fibers may be fixed to the material. Preferably, the fibers are synthetic fibers, preferably made of at least one of the group: cotton, wool, viscose, nylon, or cellulose. However, any natural or synthetic fiber may be used as long as it is bio-compatible, has comparable mechanical properties as the afore-mentioned materials, and can be applied in a suitable length. The fibers may be stitched, flocked and/or woven to the base surface.

With the inventive seal forming portion not only the seal forming surface properties in contact with a patient may be influenced in order to increase the wearing comfort but also the properties of the base material or base surface to which the fibers are fixed may be influenced in a positive manner. At least a portion of the fibers may be provided in tufts, preferably of similar length. The fibers of a tuft may be twisted. Moreover, the fibers may be looped or cut at the second end. The fibers may be provided in a multi-level arrangement. Preferably, a first portion of the fibers is provided with a first length establishing a first level of second ends. Moreover, a second portion of the fibers may be provided with a second length establishing a second level of second ends. The multi-level arrangement may further improve the resilience behavior of the seal forming portion. This may affect comfort of use and/or the leakage or sealing behavior of the patient interface.

The seal forming portion may be provided on a flexibly resilient cushion, pad, sealing lip and/or membrane of a patient interface. The fibers may be made of a material which comprises a substance to be released to the skin of a patient. Such substance releasing materials are known from the application WO 2012/131001 the content of which is incorporated by reference. The fibers may be in fluid communication with a material adapted to release substances which may be transported by the fibers to the skin of a patient. Such material may be contained in the patient interface, e.g. in a void or hollow contained therein, e.g., in the resilient cushion, pad, sealing lip and/or membrane of the patient interface.

The present technology additionally or alternatively also relates to a pad for a patient interface. The pad may comprise a resilient material layer with a seal forming portion for sealingly contacting a user's skin. The pad may comprise a seal forming portion as described above. However, the present pad may be provided with any other seal forming portion as well.

The pad may be adapted to be releasably connected to a resilient cushion. The pad may be configured as a detachable pad or may be integrally formed with the cushion. The cushion may be any kind of cushion as long as it is contoured and/or pre-shaped to approximate and/or match the contours of a user's face. The cushion may be made of an elastomeric material, for instance a silicone such as liquid silicone rubber (LSR), compression mold silicone rubber (CMSR) and/or thermoplastic elastomers (TPE) or other elastic materials.

The pad may be configured to be a disposable pad. For instance, the pad may be disposed after a certain usage. Moreover, pads of different sizes and/or with different wearing properties (e.g. softness, substance releasing, sweat transport, . . . ) may be adapted to be connected to the same cushion of a patient interface. The user may try pads with different shapes, different resilience, different tactile impressions and/or different structures together with the same cushion. That is, the pads may allow for a quick and cost-effective adaption of the patient interface to the user's needs. This may even be effected spontaneously without the need to see the retail seller or even a physician. Moreover, the pad may be tailor-made to the individual shape of the user in a cost effective way since the basic shape may be relatively simple. In principle any suitable resilient material can be used for the pad/contact surface.

The pad may be provided with a cushion contacting portion adapted to be connected with the cushion. The pad may be fixed to the cushion and the cushion contacting portion by appropriate means such as Velcro or adhesive applied to the cushion and/or pad. Alternatively, double-sided adhesive tape may be used for connecting the pad to a cushion.

The cushion contacting portion and/or the pad may have a width of at least 5 mm, preferably of at least 8 mm, and most preferably 10 mm or more. The width of the cushion contacting portion may vary around the perimeter of the face contacting contour, e.g. be narrower at the nose than at the cheeks or chin. The pad may protrude beyond the shape of the cushion, e.g., the flange portion of the cushion for at least several millimeters, preferably about 1.5 to 10.0 mm, most preferably 3.0 to 5.0 mm, preferably on each side. The pad may be provided with a sufficient width to ensure that during use only the pad and not the cushion contacts the user's face. This protrusion may be present both along the outer perimeter as well as along the inner perimeter of the pad-contacting portion of the cushion. The protrusion may also vary along the contour, e.g., a different protrusion may be provided at the nose area than at the cheeks or chin area. The cushion contacting portion may be substantially parallel to the seal forming portion of the pad. Preferably, the cushion contacting portion is located on a side opposite of the seal forming portion. The cushion contacting portion may be substantially flat and/or planar. The pad may be provided with a pad thickness between about 0.5 to 26 mm, preferably between about 1.0 to 13 mm, more preferably between about 2 and 10 mm, and most preferably between 4 and 8 mm. According to a preferred example, the pad has a thickness of about 6 mm. Such pad may be made of any of the herein discussed materials. A pad of too high thickness may hinder the contribution of the underlying cushion support structure, preferably the, e.g., I- or T-beam structure as discussed herein. A too thin pad may be less comfortable to the patients and/or also negatively influence the micro adaptation to the patient's face. The pad may be made of a foam material with a thickness between about 1.5 to 26 mm, preferably between about 3.0 and 13 mm. E.g. an open cell foam may be provided with a thickness in the range of about 3.0 to 7.0 mm. A more rigid closed cell foam, e.g., may be provided with a thickness between about 7.0 and 13.0 mm. A fabric layer may have a thickness between about 0.5 to 6 mm, preferably between about 1.0 and 3.0 mm. The pad thickness may vary along the perimeter of the pad. Moreover, the pad thickness may vary in a direction perpendicular to the direction of extension along the perimeter. The average thickness of the pad may vary between about +/−75%, preferably between about +/−50% of the average thickness of the pad measured in the direction C. The seal forming portion may be curved in a cross-sectional view (i.e. in a view perpendicular to the extension of the pad along the perimeter; cf. FIG. 8a, 8b). The pad may thus have, in a cross-sectional view, an at least two-dimensional shape. The shape of such a pad may also be called a 2.5D shape. The pad may be a substantially flat material with a bulge or a curve in the patient contacting portion. Such a pad may be easy to manufacture by punching or cutting out of a sheet material as further described below. The thickness of the pad, as referred to above, is preferably substantially thinner than the thickness of an underlying cushion structure, as discussed further herein. Such thickness may be seen in direction towards a patient's face. Preferably, the thickness of the pad is less than 70% of the cushion's thickness, more preferably, the pad's thickness is less than 50% of the cushion's thickness and more preferably, the pad's thickness is less than about 30% of the cushion's thickness.

The pad may be provided with a higher resilience than the resilience of the cushion to which the pad may be attached. The cushion may be provided with an, preferably elastic, resilience to generally adapt to the individual shape of a user's face. That is, the cushion may be adapted to provide a macro-adaption to the individual shape of a user's face. The pad may be adapted to provide an additional (micro-) adaption to the individual shape of a user's face. With other words, the patient interface may comprise a cushion providing a first resilience and a, preferably releasable, pad providing a second resilience, the second resilience being higher than the first resilience.

In conventional masks, the sealing effect is achieved by applying a locally relatively high sealing force onto the face of the patient, because the functions of macro- and micro-adaptation are both realized in one cushion and often by the same material or coupled by fully enclosing or embedding one material in another one. These functions are decoupled in the present technology. The cushion may allow for an (elastic macro-) adaptation to the shape of the patient's face. The macro-adaptation may primarily be a function of the cushion (e.g. below description of the T-shape as one preferred embodiment). The cushion may be adapted for an elastic deformation. I.e., the cushion may deform during use and may substantially return to its original shape. The pad may allow for a very fine adaptation to the face of the patient (micro-adaptation). The pad may distribute the sealing forces to a larger area in the face of the patient. Moreover, because of an improved micro-adaptation of the pad, the overall sealing force that is required may be lower while securely avoiding undesired leakages. As a result, the present technology may increase the wearing comfort for the patient. The patient interface may adapt itself to various individual contours of many different patients. The fit of the patient interface perceived by the patient may be improved. At the same time, the required number of different sizes and shapes of cushions and mask shells may be reduced. Because of the material/surface properties and due to the improved force distribution of the pad, the wearing comfort of the mask may be improved as compared to existing systems.

The pad may comprise a foam material. Preferably, the foam material is a polyurethane foam or a silicone foam. Also other bio-compatible foams may be used. The pad may comprise at least a portion which is at least partly filled with fluid. The fluid may be a liquid or a gas, preferably a gel material, air, water or oil. The pad may comprise a textile material or a combination of a textile material and a foam material. The textile material may be back molded with a foam material (foam applied to the rear side of the textile). The pad may be made of a textile material back molded with a polyurethane foam. Any polyurethanester or polyurethaneter foam may be used. For instance, medical polyurethane foam may be used which may be provided with an additional foam layer. Such foams with additionally applied foam layers could be configured as such foams used in wound dressings, i.e. to enhance wound healing. Textured fabrics may improve air circulation and may stimulate the tissue. Textured foam materials (foam material with texturing; neoprene and/or textile-coated neoprene) may be used. The pad may comprise a gel which forms a skin as well as gel enclosed in a film. The pad may comprise an adhesive material, and preferably an adhesive gel. The adhesive may be adapted to securely hold a patient interface in the application position. That is the adhesive may be adapted to fix the patient interface thereby replacing a headband means. By using such adhesive materials headbands may no longer be necessary. The pad may comprise a substance releasing material or layer adapted to release a substance to the skin of the patient. Such substance releasing material may release drugs for enhancing wound healing or releasing nurturing substances and/or aroma. The pad and pad material may be configured as the first material and the member for contacting the skin disclosed in document WO 2012/131001 A2 incorporated herewith entirely by reference. The entire seal forming portion being in contact with a user's face may be provided at the pad. The shape of the pad viewed from the face contacting side C may substantially correspond to the shape of the pad contacting portion of a cushion.

The pad, preferably the seal forming portion, may form at least a portion of, preferably the whole, perimeter of an air supply opening. The pad is, in a top view, preferably essentially triangularly shaped, preferably with round corners. The pad may contact the user's face around nose ridge (nasal bone, lateral cartilage, septum cartilage) and the lip superior or lip inferior. The pad may have other alternative configurations such as a nasal pillow configuration with a shape adapted to cover the nostrils. The pad may essentially follow the common shape of the cushion and/or patient interface (full-surface mask, nasal mask or nose cushion mask), e.g. may contact the face of the patient over the entire circumference or perimeter. However, it is also possible to apply the pad only in selected areas of the patient interface so that, e.g., sensitive areas of the face are particularly relieved. In this case, the sealing function in the remaining part of the face may be achieved by a single- or double-wall cushion in accordance with the prior art.

The pad may only provide a portion of the entire seal forming portion. At least a portion of the cushion may be single or double walled. Preferably, the cushion comprises a seal-forming portion in locations where no pad is applied. Preferably, a single- or double-walled cushion structure is applied in the area of the nose ridge. The single or double walled structure may be configured as membrane.

The pad and/or the cushion may comprise a portion of reduced stiffness in the apex of the pad. In the application position the apex of the pad may be located at the nose ridge. The portion of reduced stiffness (i.e. increased resilience) may comprise a material with a higher resilience than other portions of the pad and/or may have a different shape leading to reduced stiffness. The portion of reduced stiffness may facilitate relative movement of portions of the pad located adjacent the nose ridge in the nose region. The portion of reduced stiffness may be configured as a slit, recess, notch or slot.

The portion of reduced stiffness may facilitate, ensure and/or improve the clamping of the pad on the nose, as also described below. E.g., the slit may be provided on the inner side of the apex, i.e. the lateral side of the pad facing the nose in the application position. The slit may extend in a direction perpendicular to the peripheral direction of the pad (cf. FIG. 9a, b). The slit may extend from the face contacting side of the pad along the lateral side of the pad to the cushion contacting side of the pad. The width of the slit may increase towards its opening, i.e. towards the inner or lateral side of the pad. The slit may be chevron- or V-shaped. Also other shapes may be possible. The slit may be sized so as to allow relative movement of the pad portions located on both sides of the slit and located in the application position on both sides of the nose ridge towards each other.

The present technology additionally or alternatively also relates to a resilient cushion for a patient interface. The cushion may comprise a T- or I-beam structure with a web portion or leg and a flange portion. A first end of the web portion of the T- or I-beam shaped structure may be connected or may be connectable to a shell and/or frame of a patient interface. The flange portion may be provided at a second end of the web portion. The second end may oppose the first end of the web portion. The cushion may comprise a seal forming portion as specified above. Moreover, the flange portion of the cushion may be connected or may be connectable with a pad as disclosed above. However, the cushion of the present technology is not limited to the connection to pad having the particular design disclosed in this application and may be connected to other suitable pads. The pad may comprise the seal forming portion disclosed above. The pad may be integrally formed with the cushion.

The cushion may be made of any suitable material discussed above. The shell or frame may be made of a rigid material. For instance, a thermoplastic material, such as polybutylene-terephthalate (PBT) or polycarbonates (PC) may be used. The cushion may be clipped on the shell or frame. The cushion and the shell or frame may be connected with each other either in form-fit manner, e.g., by undercuts and/or joining part (e.g., cushion clips). The shell or frame may comprise a 2K (i.e., multi material, for example made by multi material molding such as co-molding) thermoplastic material and the cushion may comprise an elastomer material. The connection may comprise a material connection, e.g., by adhesion or multicomponent injection molding (e.g., co-molding). The frame or shell may form supported structures necessary for attaining further parts such as headbands or swivel joints (elbows).

The cushion, preferably a seal forming portion—the seal forming portion most preferably being part of a pad—forms at least a portion of, preferably the whole, perimeter of an entrance to the airways of the patient. In a top view, the cushion is preferably essentially triangularly shaped, preferably with round corners. The cushion may contact the user's face at least around nose ridge (nasal bone, lateral cartilage, septum cartilage) and the lip superior or lip inferior. The cushion may have other alternative configurations such as a nasal pillow configuration with a shape adapted to cover the nostrils. The portion of the cushion contacting around the nose is also referred to as the nose receiving portion.

At least a portion of the flange portion may be adapted to pivot, tilt and/or rock around the second end of the web portion. The flange portion may comprise two arms or limbs. The two arms or limbs may extend from the second end of the web portion in a lateral, preferably opposing, direction. The first and/or second arm may be adapted to pivot, tilt and/or rock around the second end. The first arm (inner arm) of the two arms may extend laterally inwardly from the second end of the web portion. The second arm (outer arm) may extend laterally outwardly from the second end. The two arms of the flange portion may be considered as rocker arms. The flange portion may be adapted to rock around the second end when the user's face is in contact with the mask, e.g. with the pad or with the first and/or second arm. The two "arms" of the T-shape may act against each other like a rocker. For example, if the inner "arm" is moved by contact with the face of the user into the direction of the interior of the cushion (i.e. moved towards or in the plenum chamber), the outer "arm" of the T-shape is also moved. Consequently, the inner arm drives the outer arm into contact with the face of the patient. Thus, the inner arm and/or the outer arm may be provided with a stiffness so as to transfer at least a portion of the torque caused by the contact with the face and acting on the one arm via the fulcrum located at the second end of the web portion to the other arm, thereby causing a movement of the other arm. The stiffness of the first and/or second arm may be influenced by the first/second arm width, the material used and/or other structural stiffness means. The stiffness of the first and/or second arm may vary along the perimeter of the cushion. Moreover, the relative lengths of the arm of leverage of the inside (first arm) and outside (second arm) portions may be used to affect the tilting/rocking momentum created as the pad on the flange contacts the patient's face. The relation of arms of leverage may also vary around the perimeter to achieve areas with more or less force applied. Additionally, there may be areas such as the nose, where it is preferable for the flange portion to always tilt towards the interior to achieve a seal. Yet in other areas such as e.g. the cheeks it may also be useful for the flange portion to be able to tilt outwards, e.g. to adapt to facial features such as chubby cheeks. Therefore, the preferred tilting direction in these areas may also be affected by the relative lengths of the arms of leverage, and by suitably balancing the leverage in different areas around the perimeter. The mask may be able to adapt to a wider range of facial features. The mask may easily adapt to different face geometries of different patients. The flange portion may be provided at least in the nose receiving portion of the cushion. The flange portion may be provided around the entire perimeter of the cushion (i.e. of the entrance to a patient's airways). The cushion may be provided with a resilience in the nose receiving portion of the cushion so as to clamp the cushion on the nose, preferably on the ridge of the nose. This resilience may be further promoted by either or a combination of a reduced wall thickness, a greater bulge, or a selective weakening, e.g., by means of one-sided recesses or depressions in, e.g., the web, of the T-shape structure. The web portion may be adapted to bulge in a lateral direction D. The lateral direction D is a direction extending laterally to the main axis of the web portion. The nose receiving portion may be the portion adapted to receive in the application position the nose ridge as well as adjacent parts of the nose up to the nose wings. The above-mentioned rocker function may act in the area of the nose ridge with the elasticity of the cushion, in particular with the elasticity of the legs or web portion of the T- or I-beam shaped structure, in such a manner that the nose ridge, preferably the nasal bones, lateral cartilage and/or sepal cartilage (FIG. 1e, 1g) is clamped by the pad and/or by the cushion (clamping effect, see FIGS. 5, 7a, 7b). This may lead to a particularly good sealing in this particularly sensitive part of the face. The bulging, tilting or displacement of the web portion may provide an additional resilience, particularly in the lateral direction D. The cushion and pad combination may have its highest resilience in the nose ridge area. A high resilience in this area is advantageous since it is one of the most sensitive areas in the face and the nose ridge protrudes the most deeply into the cushion, requiring the largest deflection and therefore the highest degree of adaptability.

The web portion may have a web portion length between about 1 and 50 mm, more preferably between about 5 and 30 mm, and most preferably between about 10 and 20 mm. This value may vary around the perimeter, and may also be different for nasal, full face or pillow applications. The web portion length is the length between the first and second end of the web portion. The web portion may have a web portion thickness between about 0.1 and 4 mm, more preferably between about 0.4 and 3 mm, and most preferably between about 0.5 and 2 mm. This value may vary around the perimeter, and may also be different for nasal, full face or pillow applications. The flange portion may have a flange portion width between about 1 and 50mm, more preferably between about 5 and 30 mm, and most preferably between about 10 and 20 mm. This value may vary around the perimeter, and may also be different for nasal, full face or pillow applications. Preferably, the cushion provides a large contact surface for the cushion pad. The simplified (2D-) geometry of the cushion facilitates the application of the pad. The customer may adhere the pad by himself/herself. The contact surface of the cushion is large so that there may be a sufficient surface for the connection of the pad with the cushion. The connection between pad and cushion is either releasable or non-releasable. It may be connected by adhesion or by a form-fit, e.g. by inserting the pad into a correspondingly shaped pocket of the cushion. The flange portion may have a flange portion thickness preferably between about 0.1 and 4 mm, more preferably between about 0.4 and 3 mm, and most preferably between about 0.5 and 2 mm. This value may vary around the perimeter, and may also be different for nasal, full face or pillow applications. The flange portion thickness is the thickness between the upper and lower side of the flange portion. The upper side facing the pad or comprising a sealing portion and the lower side generally facing the frame or shell. Accordingly, the flange portion thickness may be far thicker than a typical membrane. Thickness may be the same for the first and second arm of the flange portion. The momentum can be better transferred. Thickness may vary from the average thickness in key areas of the flange (e.g. thinner at the nose bridge to become more resilient). The overall width may be relatively constant. However it may be slightly thinner in critical areas such as at the side of the nose close to the eyes. The first arm and/or the second arm may have a first arm width/second arm width of between about 1 and 50 mm, more preferably between about 3 and 30 mm, and most preferably between about 5 and 15 mm. This value may vary around the perimeter, and may also be different for nasal, full face or pillow applications. The first arm width and second arm width are measured form the second end of the web portion to the respective edge of the first and second arm of the flange. The ratio of first arm width to second arm width (first arm:second arm) is between about 0.25 and 14, preferably between 0.5 and 7. The ratio of first arm to second arm results from flange width minus first arm width, in each particular area of the flange. This value may vary around the perimeter, and may also be different for nasal, full face or pillow applications. The ratio, the width of first arm and/or the width of the second arm may vary at least along a portion of the circumference of the cushion. By varying the ratio along the circumference of the cushion, either an improved support function or an improved adaptability to the patient's anatomy may be achieved. For example, a ratio of about 1 would lead to an increased support of the seal forming portion by the cushion since the web portion would almost be located in the center line of the flange portion and also in the center line of a seal forming portion, provided that flange portion and seal forming portion have about the same width and are centered to each other. The ratio of first arm to second arm widths may influence the tendency of the flange to rock inwardly or outwardly.

The geometry of the T- or I beam shaped structure may vary along the perimeter of the cushion. The ability to apply sealing force is balanced against the cushion's resilience. A high sealing force is achieved by a low curvature of the (straight, I-like shaped or "_|_" shaped) structure, whereas a high resilience is achieved by a high curvature of the (bulging, C-like shaped or "_(_" shaped) structure of the cushion.

The cushion may comprise at least one bellow structure. The cushion may also comprise at least one bulge preferably outwardly oriented and/or pre-shaped. The at least one bellow structure and/or bulge may be located in the nose receiving region of the cushion. More preferably, the bellow structure extends around the entire perimeter. The extent of bulging also may vary around the perimeter, preferably with the most prominent bulge located in the nasal area where high level of deflection is required, and preferably the least prominent bulge in the cheeks area, where the lowest level of deflection is required. Preferably, the at least one bellow structure and/or bulge is/are located in the web portion of the T- or I-beam structure. If the web portion or leg of the T- or I-beam structure is bulged towards the outside of the mask it may function as a bellow improving the ability of the patient interface to macro-adapt to the face of a patient and to clamp on the nose.

The flange portion may extend substantially perpendicular to the web portion. The flange portion may comprise a substantially planar or even side. Such side, which may also be referred to as pad supporting side, may face and/or support a pad as described above. In other words, the flange portion may not comprise elevations rising or projecting from the flat surface, for instance it may not comprise margins. However, other shapes of the flange portions may be possible. The cushion and flange portion may have corresponding shapes. The flange portion and/or the pad may be adapted to placed on each other without causing wrinkles, bends etc. in the pad. The flange portion may have a curvature only in one direction, preferably the same direction as the patient's face when viewed in a cranial direction (bottom side of mask) and/or in a caudal direction (top side of mask when applied to the patient). The flange portion may be essentially cylindrical or conical. However, a flat or a rectangular shape with large corner radii may also be possible.

At least a portion of the first arm may comprise a sealing lip. The sealing lip may be configured as a membrane. The cushion may be provided with a single- or double-wall sealing portion. The single- or double-wall portion may be located in the area of the nose ridge The nose ridge, preferably the nasal bones, lateral cartilage and/or sepal cartilage is/are the most likely location(s) where such a feature may be implemented, however, other anatomical locations may also be chosen if needed.

The cushion may be contoured or pre-shaped to approximate the contours of a user's face. The cushion may comprise a portion of reduced stiffness in the apex of the cushion. The portion of reduced stiffness may facilitate relative movement of portions of the cushion located in the application position in the nose region. One purpose of the portion of reduced stiffness may be to avoid localized high forces resulting from T- or I-shaped beam structure being stretched across the nose ridge. The portion of reduced stiffness may be configured as a slit or slot or recess. The portion of reduced stiffness may be located at least in the flange portion. The apex of the cushion may cover the nose ridge in the application position. This portion of reduced stiffness or slit or slot or recess may facilitate, ensure and/or improve the clamping of the patient interface on the nose. The slit may be provided on the inner side of the apex, i.e. the lateral side facing the nose in the application position. The slit may be provided perpendicular to the peripheral direction of the cushion. The slit may extend from the face/pad contacting surface of the flange to the surface connected to the web. The width of the slit may increase towards its opening, i.e. towards the inner side of the pad. The slit may be chevron- or V-shaped but also other shapes may be possible. The slit may be sized so as to allow relative movement of the cushion portions located on both sides of the slit towards each other.

The present technology also relates to a patient interface. The patient interface may comprise a seal forming portion, a cushion and/or a pad as described above. The present technology also relates to a forehead support of a patient interface comprising the above seal forming portion. As readily noticed by the person skilled in the art, the seal forming portion for a forehead support does not need to contact a user's skin in a sealing manner. E.g., the plurality of fibers applied to a portion of a forehead support may increase the wearing comfort for a user. The base surface and the fibers of such a forehead support may be configured as outlined above. As discussed above, the patient interface may be configured as a full-face mask, a nasal mask or a nasal pillow.

The present technology also relates to a method of manufacturing a seal forming portion, preferably for a patient interface. The method comprises the steps of: providing a base surface; providing a plurality of fibers; and fixing the plurality of fibers so that the plurality of fibers extends away from the base surface.

The base surface may be a surface of a resilient material, preferably adaptable to the contours of a user's face. The plurality of fibers may be fixed by an adhesive. The method may comprise the steps of coating the base surface and applying the plurality of fibers onto the coating. Preferably, the entire surface is provided with fibers. The resilient material may be a foam material. The resilient material may be a sheet material, preferably configured as a substantially flat and/or preferably pre-shaped material. The shape of the seal forming portion may be cut out and/or punched out of the sheet material, preferably after fixing the plurality of fibers. The pre-shaped foam may comprise an identical or similar shape than the seal forming portion. The cut out seal forming portion may be configured as a cushion pad.

Fixing fibers to a 3D shape, particularly on the final product, may be linked to manufacturing issues and may lead to increased cost and/or reduced overall quality perception. Fixing the plurality of fibers before cutting the seal forming portion and/or pads out of a resilient material may lead to lower manufacturing cost and/or to an improved overall quality of the final product. The plurality of fibers may be electrically charged before applying the plurality of fibers onto the coating. Charging the fibers may increase the uniform distribution and/or the density of the fibers.

The present technology also relates to a method of manufacturing a pad for a patient interface, preferably a patient interface as described above. The method may comprise the steps of: providing a sheet of resilient material; and punching or cutting out at least one pad from the sheet material. The resilient sheet material may be adaptable to the contour of a user's face. The punched and/or cut out pad may have a first surface adapted and/or shaped to be connected with a cushion and a second surface adapted and/or shaped so as to be adapted to contact a user's skin.

The first surface of the provided sheet material may be substantially flat and/or a second surface may be profiled. The method may comprise the step of profiling the first surface of the sheet material. The method may comprise the step of foaming the sheet of resilient material. The step of profiling may comprise the step of applying a pre-shaped structure to the first surface of the sheet material. For instance, the material to be foamed may be disposed on a conveyor belt. During foaming, an upper side of the foam material may be covered by a profiled structure moving at the same speed as the conveyor. The sheet material may be foamed/formed between the conveyor belt and the upper profiled structure to a sheet material having a substantially flat first surface and a profiled second surface. It is submitted that the profiled surface may also be obtained by any other suitable process for applying a profiled surface to a sheet material. E.g. by means of, i.a., thermoforming The pad and/or the cushion of the present application may be manufactured by a method of manufacturing as outlined in the aspects directed to the method of manufacturing a pad and/or seal forming structure in co-pending patent application EP 14 17 2727.1, the content of which is incorporated herein by reference. The method of producing a pad may also comprise one or more steps of manufacturing a seal forming portion outlined above. Providing a sheet of resilient material may comprise providing other suitable resilient materials outlined above in the description of the pad (e.g., applying textiles, fabrics, e.g., cotton fabrics,). Also the resilient material may be a combination of a textile material and a foam material. The material to be formed during the foaming process may be foamed on the cushion and on the back of a textile at the same time (back-molding).

The present technology also relates to a method of manufacturing a patient interface, preferably a patient interface as outlined above. The method may comprise the steps of providing or manufacturing a cushion, preferably a cushion as disclosed above, and applying a material to be foamed directly to the cushion. The foam material may be applied to the cushion by means of a mixing head. The mixing head may be located in the tool forming the cushion. The cushion and the foam material may be integrally formed. The cushion may be made of LSR. The foam material may be a silicone foam. The pad and the cushion of the patient interface may be integrally formed by co-molding. Alternatively or additionally, also an interlocking fit may be applied. The foam material may be provided with a profile contacting a patient face.

The present invention is not for use in negative pressure application.

The present technology may also be described by the following list of aspects:

A1. A seal forming portion (11) for contacting a user's skin for a patient interface (3000), wherein the seal forming portion comprises a base surface (111) and a plurality of fibers (112) fixed to and extending away from said base surface for, preferably sealingly, contacting a user's skin.

A2. The seal forming portion according to aspect A1, wherein the plurality of fibers extends in the application position from the base surface towards the user's skin.

A3. The seal forming portion according to aspect A1 or A2, wherein the plurality of fibers comprises fibers with a proximate end fixed to the base surface and a free distal end adapted to be in contact with a user.

A4. The seal forming portion according to any one of the preceding aspects A1 to A3, wherein the plurality of fibers extends at an angle (a) of about 60° to 120°, more preferably of about 75° to 105°, and most preferably of about 90° from the base surface.

A5. The seal forming portion according to any one of the preceding aspects A1 to A4, wherein the plurality of fibers are arranged substantially parallel to each other or may be randomly oriented.

A6. The seal forming portion according to any one of the preceding aspects A1 to A5, wherein the plurality of fibers are arranged at a density between about 10 to 100 g/m$^2$, preferably between about 20 and 65 g/m$^2$, and most preferably between about 30 and 45 g/m$^2$.

A7. The seal forming portion according to any one of the preceding aspects A1 to A6, wherein the fiber has a length ($l_{112}$) measured from the proximate end to the distal end between about 0.01 and 5.0 mm, more preferably between about 0.05 and 2.0 mm and most preferably between about 0.1 and 1.0 mm.

A8. The seal forming portion according to any one of the preceding aspects A1 to A7, wherein the fiber a titre (yarn count) value [dtex] in a range of about 0.01 to 10 dtex, more preferably about 0.1 to 5 dtex, most preferably of about 0.5 to 2 dtex, wherein the Dtex is measured in g/10.000 m.

A9. The seal forming portion according to any one of the preceding aspects A1 to A8, wherein seal forming portion is located around the entire perimeter, and wherein the leakage of the seal forming portion around the entire perimeter amounts to between about 2 l/min and 60 l/min, preferably between about 5 l/min to 30 l/min.

A10. The seal forming portion according to any one of the preceding aspects A1 to A9, wherein the seal forming portion forms a perimeter of an entrance to the airways of the patient.

A11. The seal forming portion according to any one of the preceding aspects A1 to A10, wherein the plurality of fibers have a varying resilience along the perimeter of the seal forming portion.

A12. The seal forming portion according to any one of the preceding aspects A1 to A11, wherein the plurality of fibers provide a higher resilience in the nose ridge area than in other areas of the seal forming portion.

A13. The seal forming portion according to any one of the preceding aspects A1 to A12, wherein the plurality of fibers are fixed to the base surface by an adhesive (113).

A14. The seal forming portion according to aspect A13, wherein the adhesive (113) is coated on the base surface.

A15. The seal forming portion according to any one of the preceding aspects A1 to A14, wherein seal forming portion is made of a resilient material (114), preferably adaptable to the contour of a user's face.

A16. The seal forming portion according to any one of the preceding aspects A1 to A15, wherein the seal forming portion is made of a foamed material, preferably an open cell foam.

A17. The seal forming portion according to any one of the preceding aspects A1 to A15, wherein the seal forming portion is made of a textile material, preferably a resilient textile material.

A18. The seal forming portion according to aspect A17, wherein the plurality of fibers are made of at least one of the group: cotton, wool, viscose, nylon, or cellulose.

A19. The seal forming portion according to any one of the preceding aspects A1 to A18, wherein the plurality of fibers are felted, braided, combed, brushed, frayed, stitched, flocked and/or woven to the base surface, preferably wherein the plurality of fibers are flocked on a foam material by an adhesive.

A20. The seal forming portion according to any one of the preceding aspects A1 to A19, wherein at least a portion the fibers are provided in a plurality of tufts.

A21. The seal forming portion according to aspect A20, wherein the fibers of a tuft are twisted.

A22. The seal forming portion according to any one of the preceding aspects A3 to A21, wherein at least a portion of the fibers are looped at the distal end.

A23. The seal forming portion according to any one of the preceding aspects A3 to A22, wherein at least a portion of the fibers are cut at the free end.

A24. The seal forming portion according to any one of the preceding aspects A3 to A23, wherein the fibers are provided in a multilevel arrangement (112"), preferably wherein a first portion of fibers are provided with a first length ($l_{112a}$) establishing a first level of distal ends, and wherein a second portion of fibers are provided with a second length ($l_{112b}$) establishing a second level of distal ends.

A25. The seal forming portion according to any one of the preceding aspects A1 to A24, wherein the plurality of fibers are made of or are in fluid communication with a material comprising a substance, wherein the material is adapted to release the substance to the skin of a patient.

A26. The seal forming portion according to any one of the preceding aspects A1 to A25, wherein the seal forming portion is provided on and/or forms part of a preferably resilient cushion, pad, sealing lip and/or membrane.

B1. A pad (10) for a patient interface (3000) comprising a resilient material layer having a seal forming portion (11) for sealingly contacting a user's skin, wherein the pad is adapted to be connected to a resilient cushion (20), preferably contoured to approximate the contours of a user's face.

B2. The pad according to aspect B1, wherein the pad is provided with a cushion contacting portion (13) adapted to be connected with the cushion.

B3. The pad according to aspect B1 or B2, wherein the cushion contacting portion and/or wherein the pad has a width ($w_{10}$) of at least about 5 mm, preferably of at least about 8 mm, and most preferably of at least about 10 mm, and/or wherein the pad protrudes beyond the shape of the cushion, e.g. the flange portion of the cushion for at least several millimeters, preferably about 1.5 to 10.0 mm, most preferably about 3.0 to 5.0 mm, preferably on each side.

B4. The pad according to any one of the preceding aspects B1 to B3 and a cushion, wherein the cushion contacting portion width ($w_{13}$) is within about 50% to 100%, preferably within about 75% to 100%, and more preferably between about 85% and 100% of width of the flange portion ($w_{26}$).

B5. The pad according any one of the preceding aspects B2 to B4, wherein the cushion contacting portion is substantially parallel to the seal forming portion of the pad, and/or wherein the cushion contacting portion is substantially flat.

B6. The pad according to any one of the preceding aspects B1 to B5, wherein the pad, which preferably is, is provided with or comprises a foam material, which preferably has a pad thickness ($t_{10}$) between about 1.5 to 26 mm, preferably between about 3.0 and 13 mm, more preferably between about 2 and 10 mm, and most preferably between 4 and 8 mm.

In this embodiment, the foam material preferably has a flocked surface, preferably being the seal forming portion.

B7. The pad according to any one of the preceding aspects B1 to B6, wherein the seal forming portion is curved in a cross sectional view.

B8. The pad according to any one of the preceding aspects B1 to B7 and a cushion, wherein the pad is provided with a higher resilience than the resilient cushion, the resilient cushion preferably being provided with a resilience to generally adapt to the individual shape of a user's face.

B9. The pad according to any one of the preceding aspects B1 to B8 and a cushion, wherein the pad is adapted to provide a micro-adaption to the individual shape of a user's face, and wherein the cushion is adapted to provide a macro-adaption to the individual shape of a user's face.

B10. The pad according to any one of the preceding aspects B1 to B9, wherein the pad comprises a foam material.

B11. The pad according to aspect B10, wherein the foam material is a polyurethane foam or a silicone foam.

B12. The pad according to any one of the preceding aspects B1 to B11, further comprising the seal forming portion in accordance to any one of aspects A1 to A26, wherein the resilient material layer of the pad (10) preferably constitutes the base surface (111) of the seal forming portion.

B13. The pad according to any one of the preceding aspects B1 to B12, wherein at least a portion of the pad is at least partly filled with fluid.

B14. The pad according to aspect B13, wherein the fluid is a liquid or a gas, preferably a gel material, air, water or oil.

B15. The pad according to any one of the preceding aspects B1 to B14, wherein the pad comprises a textile material or a combination of a textile material and foam material, preferably a textile material back molded with foam material.

B16. The pad according to any one of the preceding aspects B1 to B15, wherein the pad comprises an adhesive material, preferably an adhesive gel. Said adhesive material being preferably provided on two opposite sides of the pad, preferably on all sides of the pad.

B16b. The pad according to any one of the preceding aspects B1 to B16, wherein the pad is provided with an adhesive coating on two opposing sides thereof, the opposing adhesive layers touching each other, preferably forming a bond or weld where they touch.

B16c. The pad according to any one of the preceding aspects B1 to B16b, wherein the pad is non-permeable for air.

B17. The pad according to any one of the preceding aspects B1 to B16c, wherein the pad comprises a substance releasing material layer adapted to release a substance to the skin of a patient.

B18. The pad according to any one of the preceding aspects B1 to B17, wherein the entire seal forming portion being in contact with the user's face is provided at the pad.

B19. The pad according to any one of the preceding aspects B1 to B18 and a cushion, wherein the shape of the pad viewed from the face contacting side (C) substantially corresponds to the shape of the pad contacting portion of the cushion.

B20. The pad according to any one of the preceding aspects B1 to B19, wherein the pad only provides a portion of the entire seal forming portion.

B20b. The pad according to any one of the preceding aspects B1 to B20, wherein the pad provides the only seal forming portion.

B20c. The pad according to any one of the preceding aspects B1 to B20b, wherein the pad comprises 4 layers, preferably a foam layer, two adhesive layers being provided on opposing sides of the foam layer, and a fiber layer, being provided on one of the adhesive layers.

B21. The pad according to aspect B20 and a cushion, wherein at least a portion of the cushion is single- or double-walled with a seal forming portion, preferably in the area of the nose ridge, and preferably one wall portion configured as a membrane.

B22. The pad according to any one of the preceding aspects B1 to B21, wherein the pad comprises a portion of reduced stiffness, preferably in the apex (P) of the pad, preferably to facilitate relative movement of portions of the pad adjacent the nose region.

B23. The pad according to aspect B22, wherein the portion of reduced stiffness is configured as a slit (15).

C1. A resilient cushion (20) for a patient interface (3000), the cushion comprising at least along a portion of the circumference a first structure (22) having an elongate section (24) joined with at least one end section (26) oriented substantially perpendicular or at an angle to the elongate section (24),
wherein a first end (A) of the elongate section (24) is connected or connectable to a frame member (30), and wherein the end section (26) is provided at an opposing second end (B) of the elongate section (24).

C2 The cushion according to aspect C1, wherein the first structure (22) is an elongate, preferably straight structure (24) joined at one of its ends with at least one elongate, preferably straight end section (26), oriented substantially perpendicular or at an angle (to the elongate section (24)

C3 The cushion according to aspect C1 or C2, wherein the first structure (22) is a T- or I-beam shaped structure (22), wherein the elongate section (24) is the web portion (24) and the end section (24) is the flange portion (26).

C4 The cushion according to aspect C1 to C3, wherein the frame member (30) is in the form of a shell (30).

C5 The cushion according to any one of aspects C1 to C4, further comprising a seal forming portion (11) in accordance with any one of aspects A1 to A26.

C6. The cushion according to any one of aspects C1 to C5, wherein the flange portion is connected or connectable with a pad (10) comprising a seal forming portion (11).

C7. The cushion according to aspect C6, wherein the pad (10) is a pad in accordance with any one of aspects B1 to B23.

C8. The cushion according to any one of the preceding aspects C1 to C7, wherein at least a portion of the flange portion is adapted to rotate relative to the second end (B) of the web portion.

C9. The cushion according to any one of the preceding aspects C1 to C8, wherein at least a portion of the flange portion is adapted to rotate relative to, to pivot and/or to rock around the second end (B) of the web portion.

C10. The cushion according to any one of the preceding aspects C1 to C9, wherein the flange portion comprises two arms (261, 262) extending from the second end (B) of the web portion in a lateral direction, and preferably wherein the first and/or second arm is/are adapted to rotate relative to, to pivot and/or to rock around the second end (B).

C11. The cushion according to aspect C10, wherein a first (261) of the two arms (261, 262) extends inwardly from the second end (B) of the web portion (24).

C12. The cushion according to any one of the preceding aspects C1 to C11, wherein the flange portion (26) is adapted to rock around the second end (B), the two arms (261, 262) of the flange portion (26) being the rocker arms, wherein the flange portion (26) is adapted to rock around the second end (B) when the user's skin is in contact, preferably via a portion a the pad (10), with the first and/or second arm (261, 262).

C13. The cushion according to any one of the preceding aspects C1 to C12, wherein the flange portion (26) is provided at least in the nose receiving portion of the cushion.

C14. The cushion according to any one of the preceding aspects C1 to C13, wherein the flange portion (26) is adapted to rock around the second end (B), and wherein the cushion (20), particularly the web portion 24, is provided with a resilience in the nose receiving portion so as to clamp the cushion on the ridge of the nose.

C15. The cushion according to any one of the preceding aspects C1 to C14, wherein the web portion (24) is adapted to bulge in a lateral direction (D).

C16. The cushion according to any one of the preceding aspects C1 to C15, wherein the cushion comprises at least one bellow structure and/or, preferably outwardly oriented and preshaped, bulge, preferably located in the nose receiving region and/or preferably located in the web portion (24).

C17. The cushion according to any one of the preceding aspects C1 to C16, wherein the flange portion (26) extends substantially perpendicular to the web portion (24).

C18. The cushion according to any one of the preceding aspects C1 to C17, wherein the flange portion (26) comprises a substantially planar side facing the pad.

C19. The cushion according to any one of the preceding aspects C1 to C18, wherein the web portion (24) has a web portion length ($l_{24}$) between 1 and 50 mm, more preferably between about 5 and 30 mm, and most preferably between about 10 and 20 mm.

C20. The cushion according to any one of the preceding aspects C1 to C19, wherein the web portion (24) has a web portion thickness ($t_{24}$) between about 0.1 and 4 mm, more preferably between about 0.4 and 3 mm, and most preferably between about 0.5 and 2 mm.

C21. The cushion according to any one of the preceding aspects C1 to C20, wherein the flange portion has a flange portion width ($w_{26}$) between about 1 and 50 mm, more preferably between about 5 and 30 mm, and most preferably between about 10 and 20 mm.

C22. The cushion according to any one of the preceding aspects C1 to C21, wherein the flange portion has a flange portion thickness ($t_{261}$), the first arm (261) has a first arm thickness ($t_{261}$), and/or the second arm (262) has a second arm thickness ($t_{262}$), preferably between about 0.1 and 4 mm, more preferably between about 0.4 and 3 mm, and most preferably between about 0.5 and 2 mm.

C23. The cushion according to any one of the preceding aspects C1 to C22, wherein first arm (261) has a first arm width ($w_{261}$) between about 1 and 50 mm, more preferably between about 3 and 30 mm, and most preferably between about 5 and 15 mm.

C24. The cushion according to any one of the preceding aspects C1 to C23, wherein the second arm (262) has a second arm width ($w_{262}$) between about 1 and 50 mm, more preferably between about 3 and 30 mm, and most preferably between about 5 and 15 mm.

C25. The cushion according to any one of the preceding aspects C1 to C24, wherein at least one dimension of the dimensions web portion thickness ($t_{24}$), web portion length ($l_{24}$), flange portion thickness ($t_{26}$), flange portion width ($w_{26}$), first arm width ($w_{261}$), and/or second arm width ($w_{262}$) vary at least along a portion of the circumference of the cushion.

C26. The cushion according to any one of the preceding aspects C1 to C25, wherein the ratio of first arm width ($w_{261}$) to second arm width ($w_{262}$) is between about 0.25 to 14, preferably between about 0.5 to 7.

C27. The cushion according to aspect C26, wherein the ratio varies at least along a portion of the circumference of the cushion.

C28. The cushion according to any one of the preceding aspects C1 to C27, wherein at least a portion of the cushion, preferably the first arm, comprises a sealing lip, preferably configured as a membrane.

C29. The cushion according to aspect C28, wherein the cushion (20) is provided with a single- or double-wall sealing portion, preferably in the area of the nose ridge.

C30. The cushion according to any one of the preceding aspects C1 to C29, wherein the cushion (20) is contoured to approximate the contours of a user's face.

C31. The cushion according to any one of the preceding aspects C1 to C30, wherein the cushion (20) comprises a portion of reduced stiffness (15) in the apex (P) of the cushion (20), preferably to facilitate relative movement of portions of the cushion (20) adjacent the nose region.

C32. The cushion according to aspect C31, wherein the portion of reduced stiffness is configured as a slit (15), the slit (15) preferably located at least in the flange portion (26).

C33. The cushion according to any one of the preceding aspects C1 to C32, wherein the first arm (261), preferably also the second arm (262), comprises at least two portions (261-1, 261-2; 262-1, 262-2) made of different materials, preferably a first portion (261-1;262-1) located proximal to the second end (B) of the web portion (24) in a cross-sectional view made of a first material and a second portion (261-2;262-2) located distal to the second end (B) of the web portion (24) in a cross-sectional view made of a second material, wherein most preferably the first material is less resilient than the second material.

C34. The cushion according to any one of the preceding aspects C1 to C33, the cushion being made from silicone, preferably liquid silicone rubber.

D1. A patient interface (3000) comprising
the seal forming portion (11) in accordance with any one of the preceding aspect A1 to A26,
the pad (10) in accordance with any one of the preceding aspect B1 to B23, preferably provided on the end surface (26) and/or
the cushion (20) accordance with any one of the preceding aspect C1 to C33, the end surface (26) preferably being adapted for receiving a pad, preferably in accordance with any one of the preceding aspect B1 to B23.

D2. The patient interface of aspect D1 wherein the patient interface (3000) is a full-face mask, a nasal mask or a nasal pillow.

D3. A forehead support (3700) comprising
the seal forming portion (11) in accordance with any one of the preceding aspects A1 to A26, and/or
the pad (10) in accordance with any one of the preceding aspects and B1 to B23.

E1. A method of manufacturing a seal forming portion (11) for a patient interface (3000), preferably according to any one of the preceding aspects A1 to A26, comprising one or more of the steps:
providing a base surface being a surface of a resilient material (114) adaptable to the contour of a user's face;
providing a plurality of fibers (112); and
fixing the plurality of fibers so that the plurality of fibers extends away from the base surface.

E2. The method of aspect E1, wherein said plurality of fibers is fixed by an adhesive.

E3. The method of aspect E2, wherein the fixing comprises the steps:
coating the base surface; and/or
applying the plurality of fibers onto the coating.

E4. The method according to any one of the preceding aspects E1 to E3, wherein the resilient material is foam material.

E5. The method according to any one of the preceding aspects E1 to E4, wherein the resilient material (114) is a substantially flat and/or pre-shaped sheet material.

E6. The method according to aspect E5, wherein the shape of the seal forming portion is cut out or punched out of the sheet material after fixing the plurality of fibers.

E7. The method according to any one of the preceding aspects E3 to E6, wherein the plurality of fibers are electrically charged before applying the plurality of fibers onto the coating.

F1. A method of manufacturing a pad (10) for a patient interface (3000), preferably according to any one of the preceding aspects B1 to B23, comprising the steps:
providing a resilient sheet material adaptable to the contour of a user's face;
punching or cutting out at least one pad (10) from the sheet material;
wherein the at least one punched or cut-out pad (10) has a first surface shaped to be connected with a cushion in a cushion contacting portion (13) of the pad (10) and a second surface shaped so as to be adapted to contact an user's skin at a seal forming portion (11) of the pad (10).

F2. The method of aspect F1, additionally comprising the step of foaming the sheet of resilient material.

F3. The method of aspect F1 or F2, wherein the first surface is substantially flat and/or wherein the second surface is profiled.

F4. The method according to any one of the preceding aspects F1 to F3, additionally comprising the step of profiling the first surface of the sheet material.

F5. The method of aspect F4, wherein the profiling comprises the step of applying a pre-shaped structure to the first surface.

F6. The method according to any one of the preceding aspects F1 to F5, wherein the sheet is provided with a texturing or a textile.

F7. The method according to any one of the preceding aspects F1 to F6, additionally comprising the step of manufacturing a seal forming portion (11) in accordance with any one of the preceding aspects E1 to E7.

G. A method of manufacturing a patient interface (3000), preferably according to preceding aspect D1 or D2, comprising the steps:
 providing a cushion (20) according to any one of the preceding aspects C1 to C33 and
 applying a material to be foamed during the foaming process directly to the cushion (20), wherein the foamed material forms a pad, preferably according to any one of aspects B1 to B23.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Patient Interface

Figure 2:
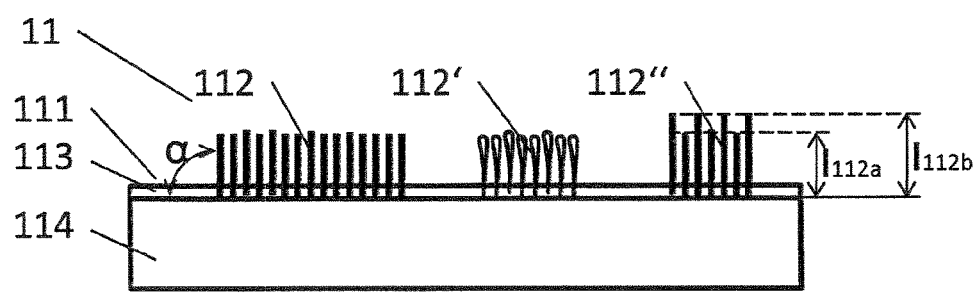

FIGS. 2 to 12 show a patient interface 3000 in accordance with the present technology, wherein FIG. 2 shows preferred examples of seal forming portions.

Figure 3:
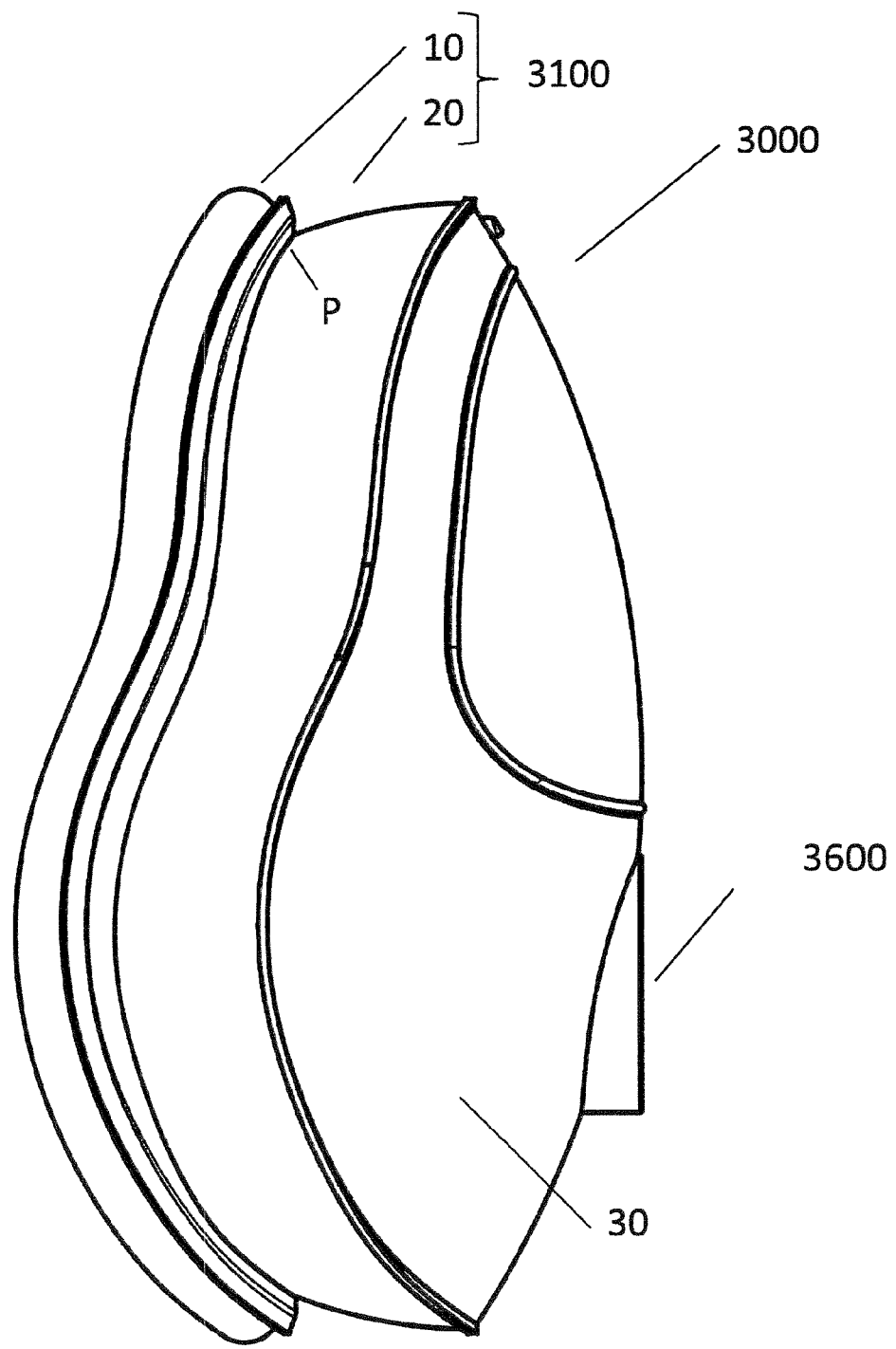

FIG. 3 shows a side view of a preferred patient interface comprising a pad arranged on a cushion of a patient interface.

Figure 4:
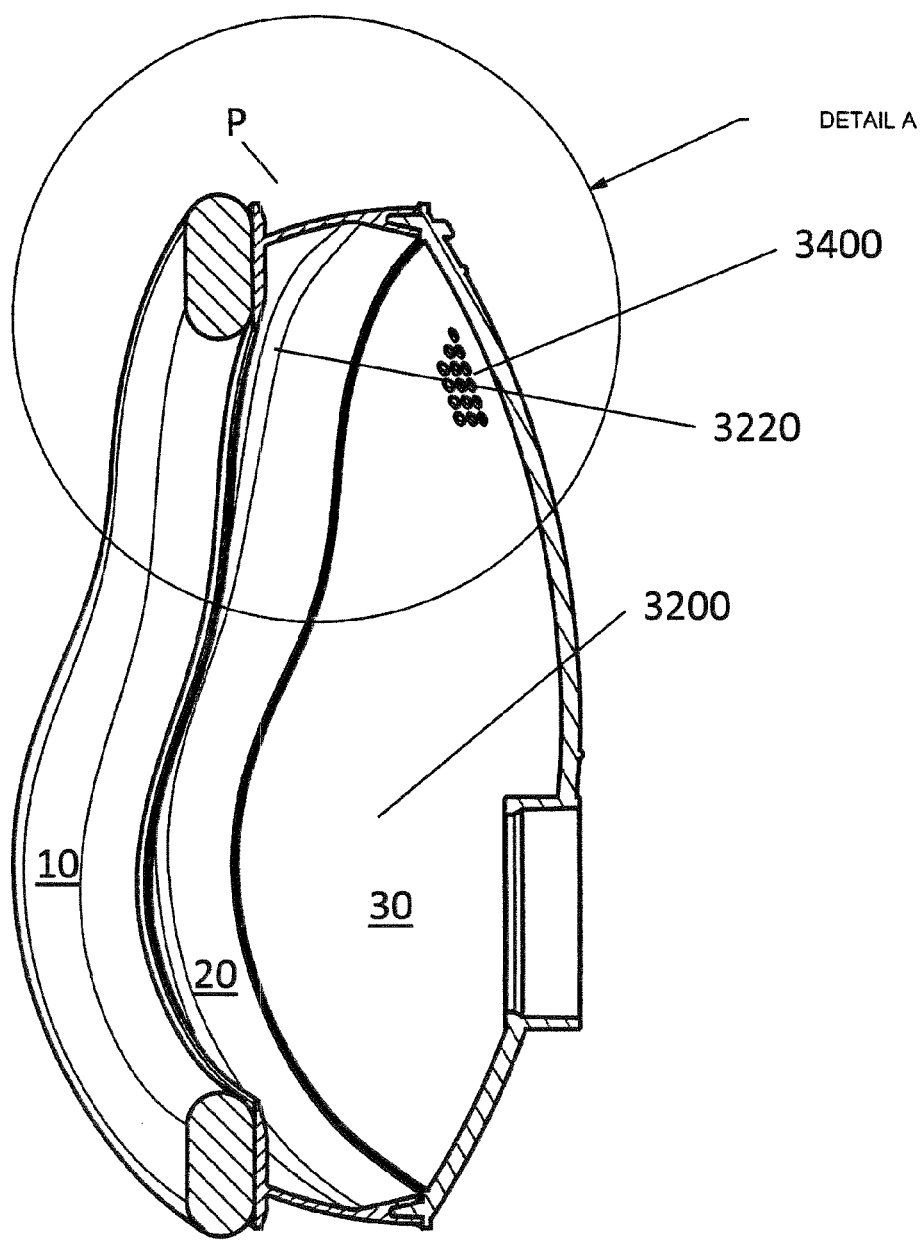

FIG. 4 shows a cross sectional view of a preferred patient interface comprising a pad arranged on a cushion of a patient interface.

Figure 5:
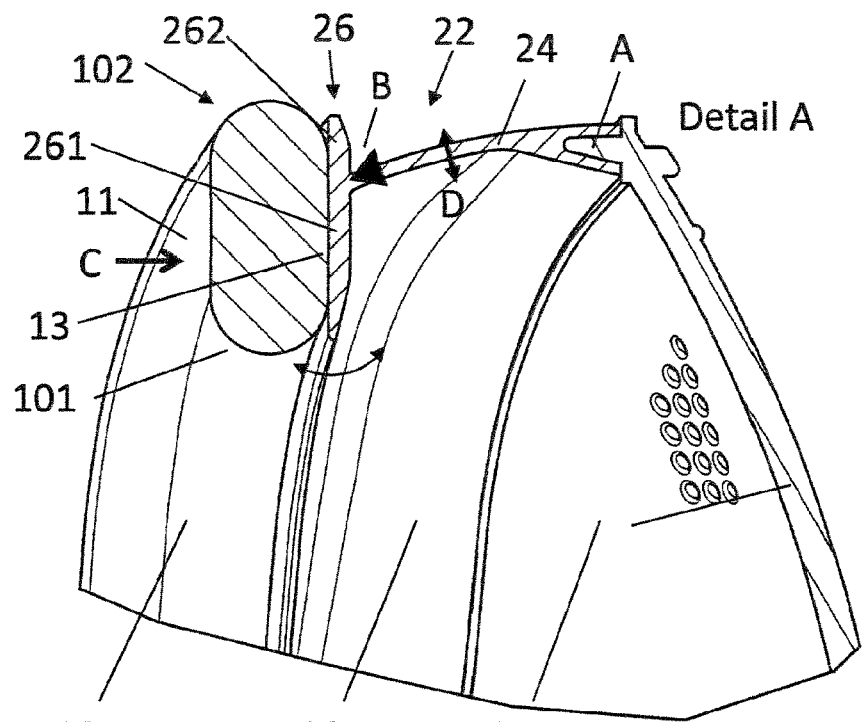
Figure 6:
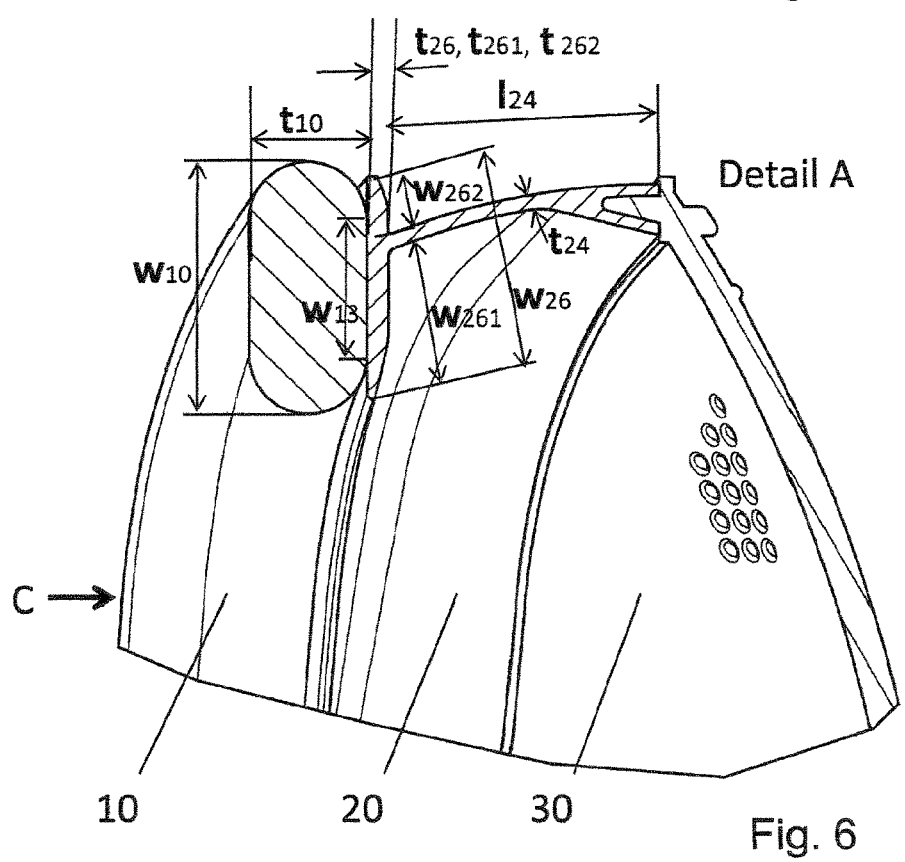

FIGS. 5 and 6 show an enlarged portion of a preferred patient interface comprising a pad arranged on a cushion of a patient interface.

Figure 7A:
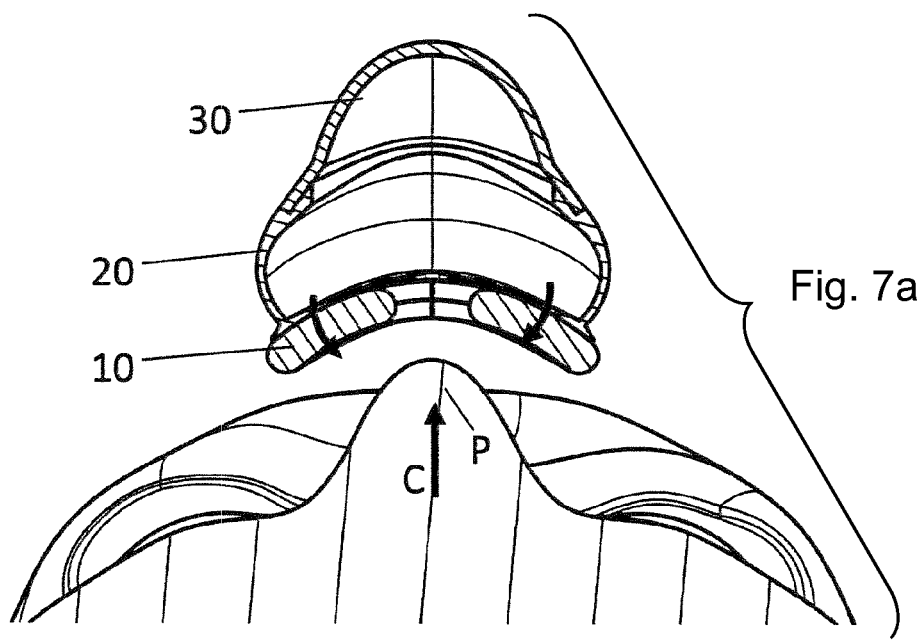

FIG. 7a shows a sectional view of the mask position seen from the chin side to illustrate the situation of the patient's nose just before biasing the mask cushion inward to achieve the clamping effect.

Figure 7B:
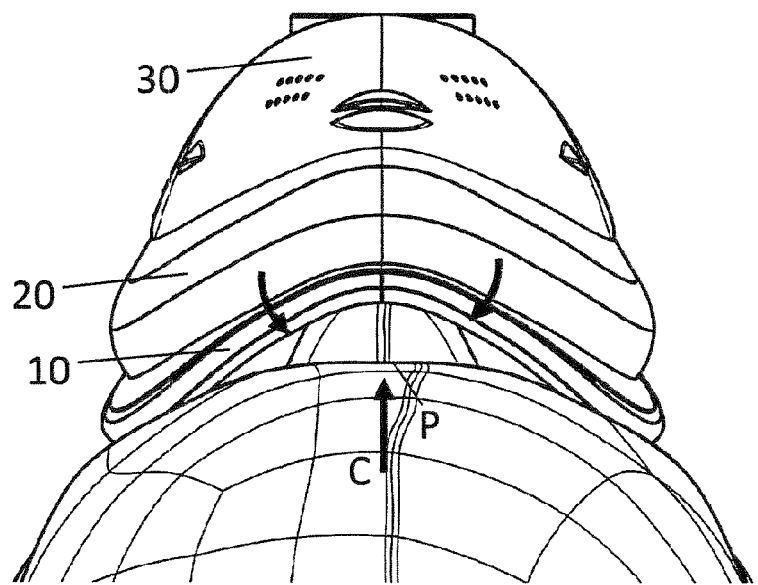

FIG. 7b shows a non cross-sectional view of the same mask position being applied to the patient's face, seen from the forehead side The arrows indicate deformation and/or movement of the pad and cushion at the nose ridge, preferably at the nasal bones, lateral cartilage and/or sepal cartilage, of the patient.

FIGS. 8a and 8b show cross sectional views of a pad at a position as indicated in FIG. 9b, FIGS. 9a and 9b show top views on (parts of) a preferred sealing flange portion.

Figure 10C:
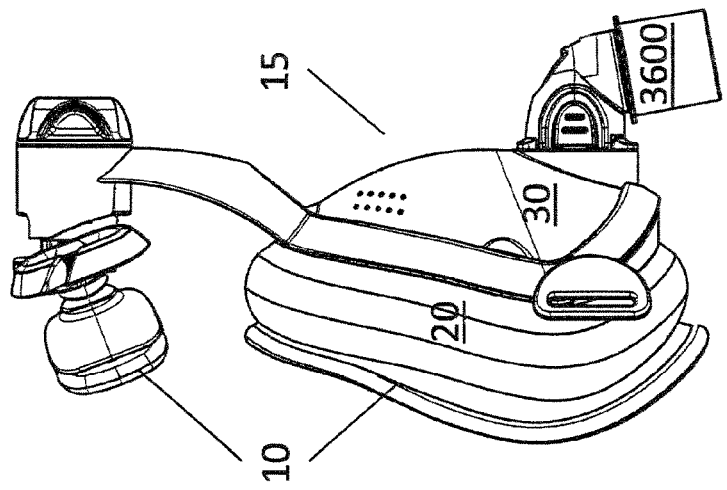
Figure 10B:
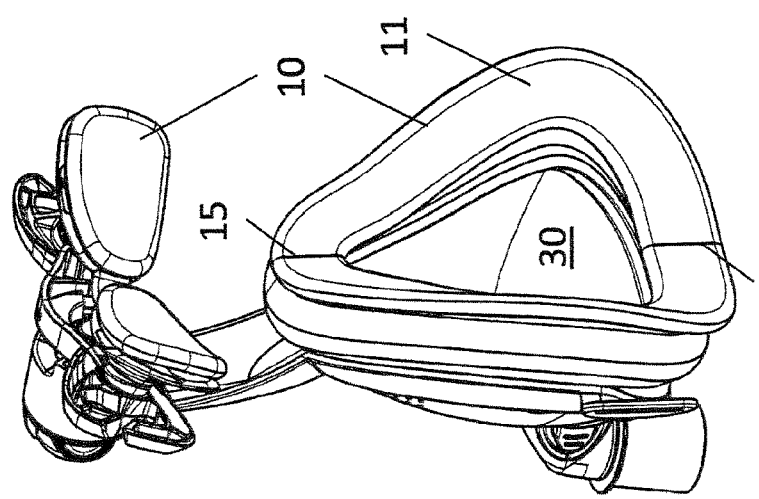
Figure 10A:
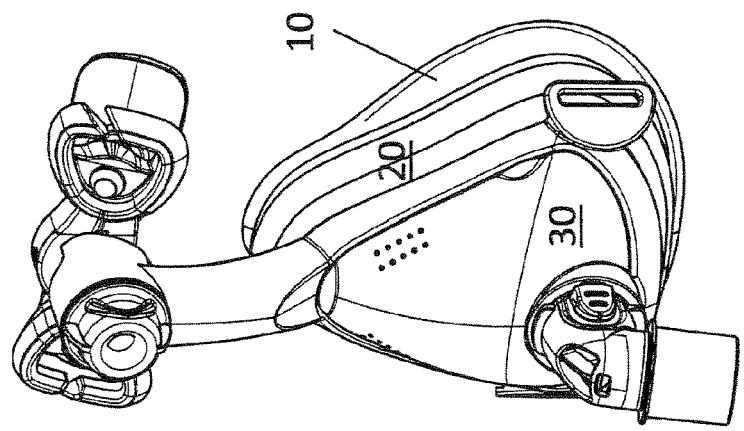

FIGS. 10a-10C shows three dimensional views of an exemplary mask in line with the present technology wherein
 FIG. 10a shows a diagonal front view.
 FIG. 10b shows a diagonal back view.
 FIG. 10c shows a side view.

FIG. 11a shows a side view of a cushion and pad according to the present technology.
 FIG. 11b shows a cross sectional side view.
 FIG. 11c shows detail A of FIG. 11b.
 FIG. 11d shows detail B of FIG. 11b.

Figure 12:
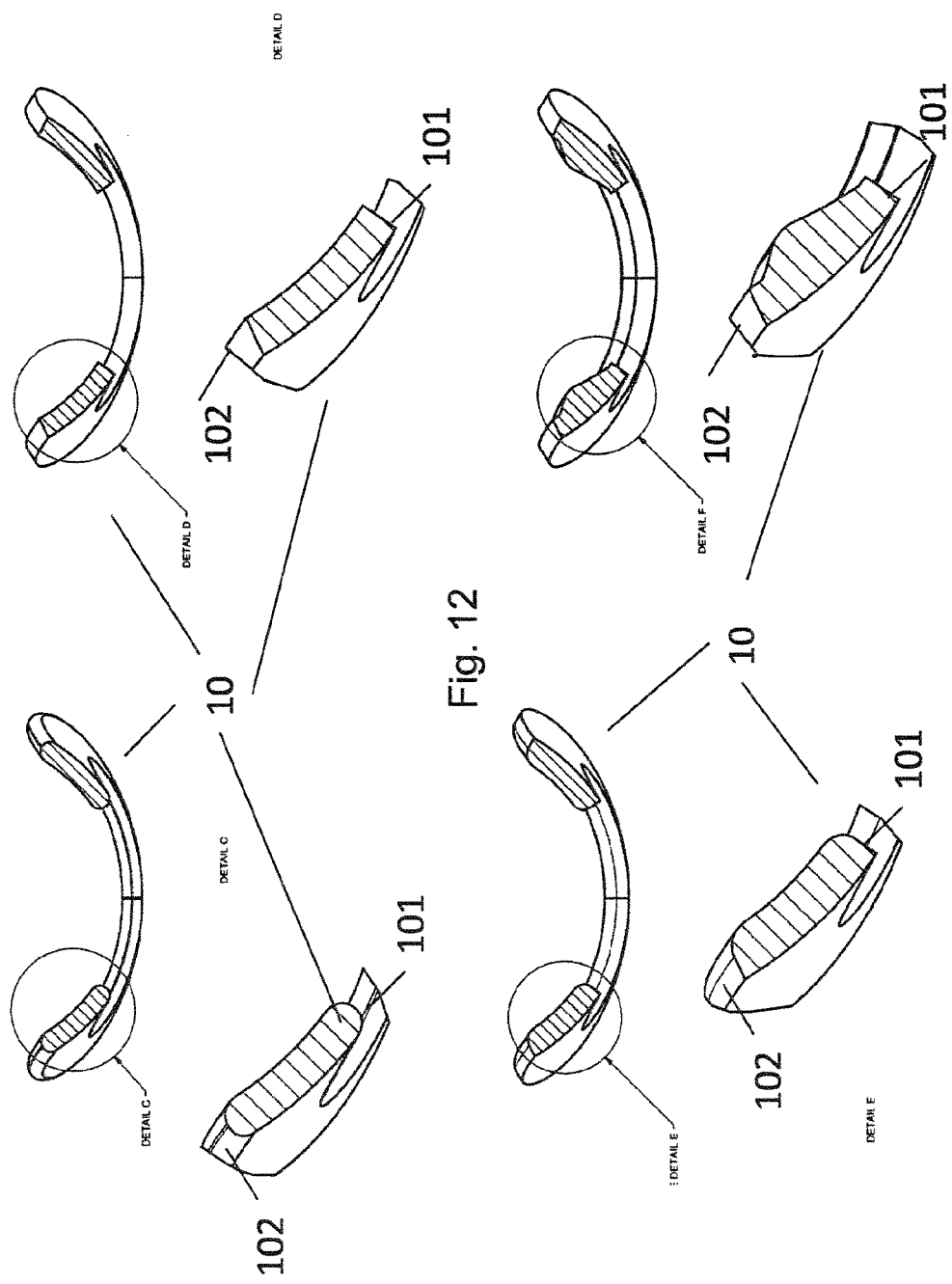

FIG. 12 shows different three dimensional cross sectional views of preferred pads of the present technology and enlarged details thereof.

Figure 13:
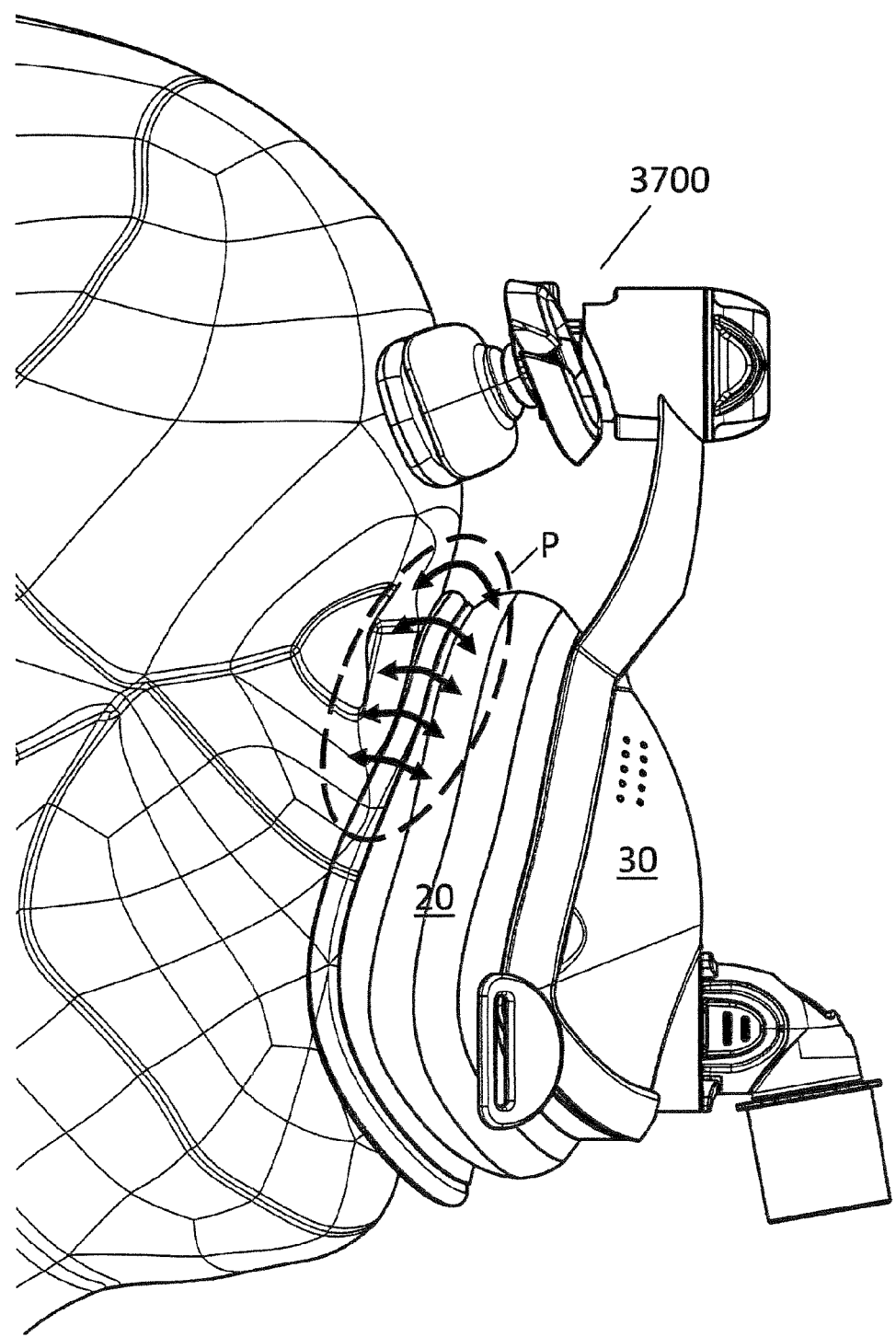

FIG. 13 shows a side view of the mask in use. The patient interface 3000 with a frame member 30 may be, preferably removably, held by a frame element comprising the forehead support 3700. The curved arrows indicate the movement of the upper portion of the pad 10 and/or the cushion 20, i.e. the movement of the apex P, while being positioned on the nose. The rotational, rocking and/or pivoting movement inwards to the plenum chamber 3200 may occur simultaneously to the movement in the direction D depicted in FIG. 5. The portion contacting the nose ridge as well as directly adjacent left and/or right portions of the pad 10 and/or cushion 20 may rotationally move upon insertion of the nose into the plenum chamber 3200. The direction of the movement of the portion contacting the nose ridge as well as directly adjacent left and/or right portions may differ. The clamping region (here shown as a dashed line) may also be located at other locations not depicted in FIG. 13.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

Treatment Systems

The present technology comprises apparatus for treating a respiratory disorder. The apparatus may comprise a flow generator or blower for supplying pressurised respiratory gas, such as air, to the patient via an air delivery tube leading to a patient interface 3000.

Nasal CPAP for OSA

The present technology may comprise a method of treating Obstructive Sleep Apnea in a patient by applying nasal continuous positive airway pressure to the patient.

A supply of air at positive pressure may be provided to the nasal passages of the patient via one or both nares.

In certain embodiments of the present technology, mouth breathing is limited, restricted or prevented. Also, as will be appreciated, CPAP treatment may be provided via the patient's mouth.

Patient Interface 3000

Figure 1A:
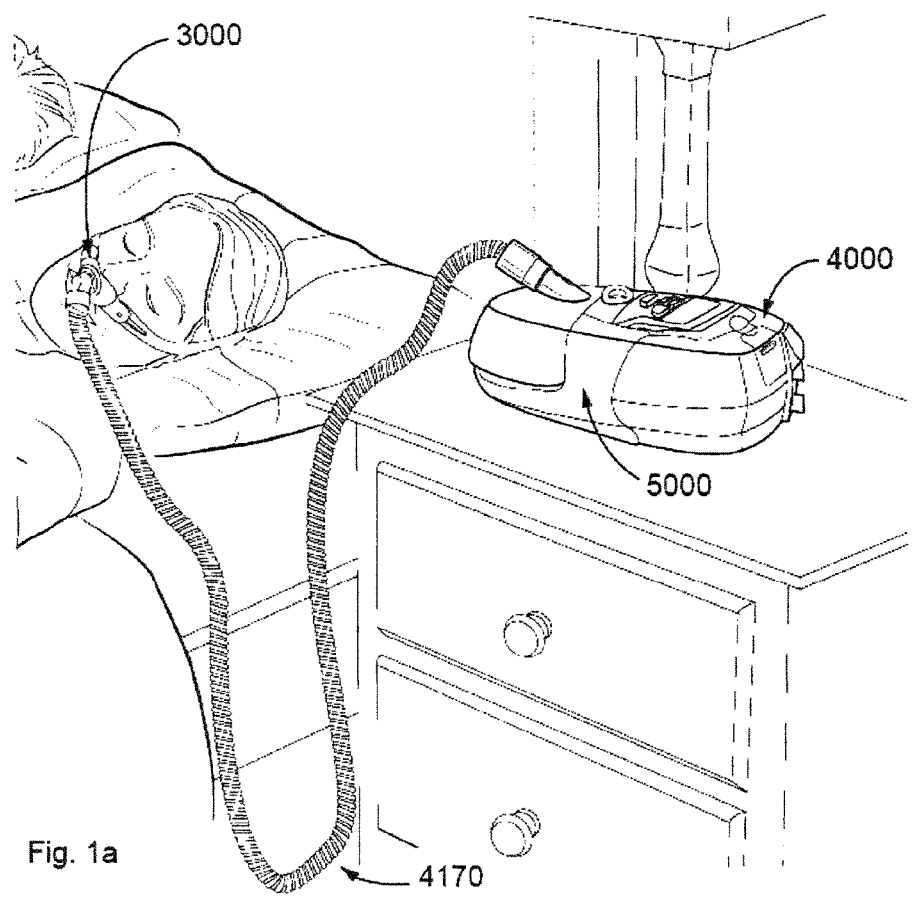
FIG. 1a shows a system in accordance with the present technology. A patient wearing a patient interface 3000, receives a supply of air at positive pressure from a PAP device 4000. Air from the PAP device is humidified in a humidifier 5000, and passes along an air circuit 4170 to the patient.
Figure 1B:
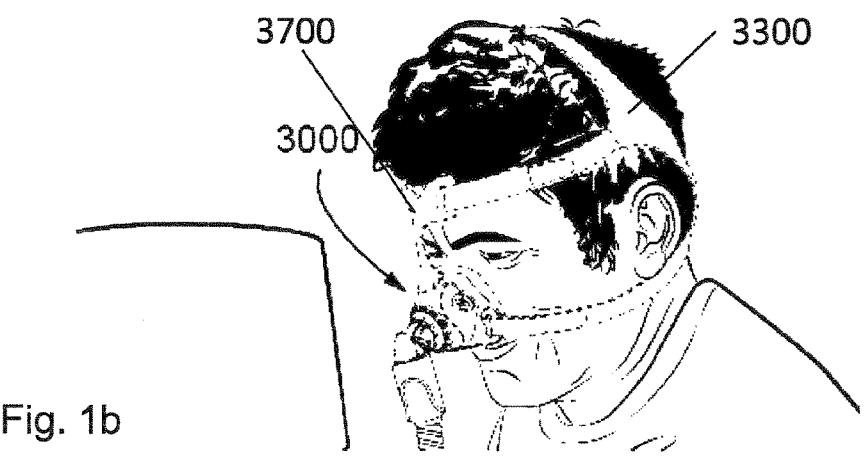
FIG. 1b shows a PAP device in use on a patient with a nasal mask.
Figure 1C:
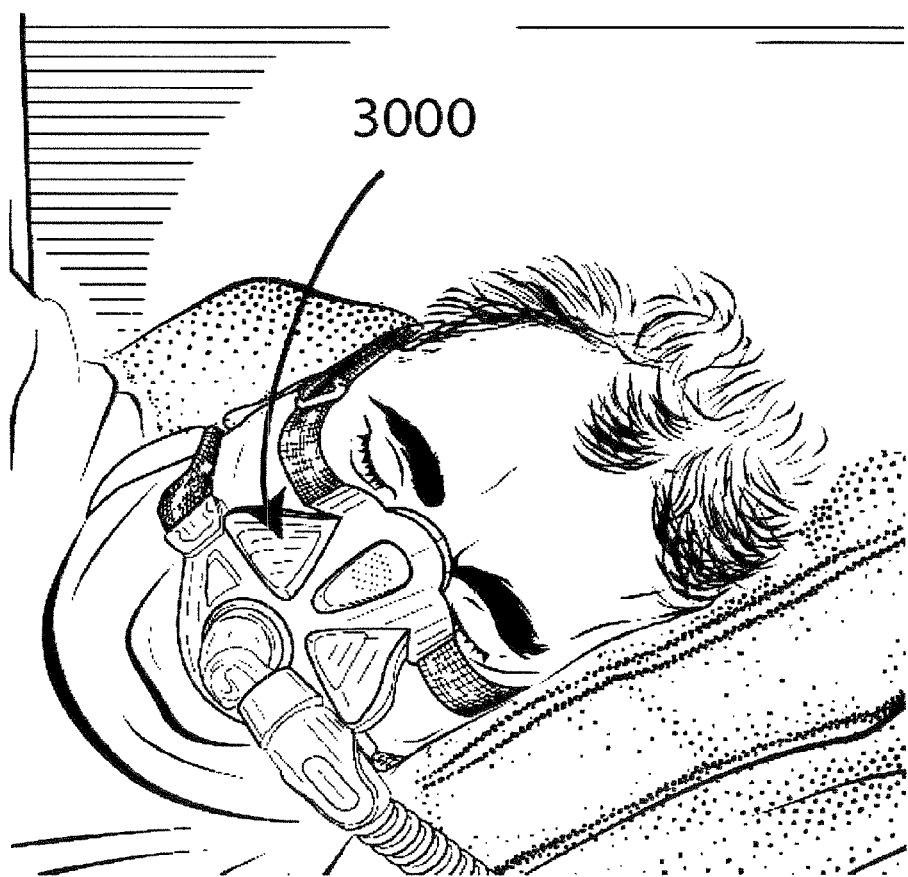
FIG. 1c shows a PAP device in use on a patient with a full-face mask.
Figure 1D:
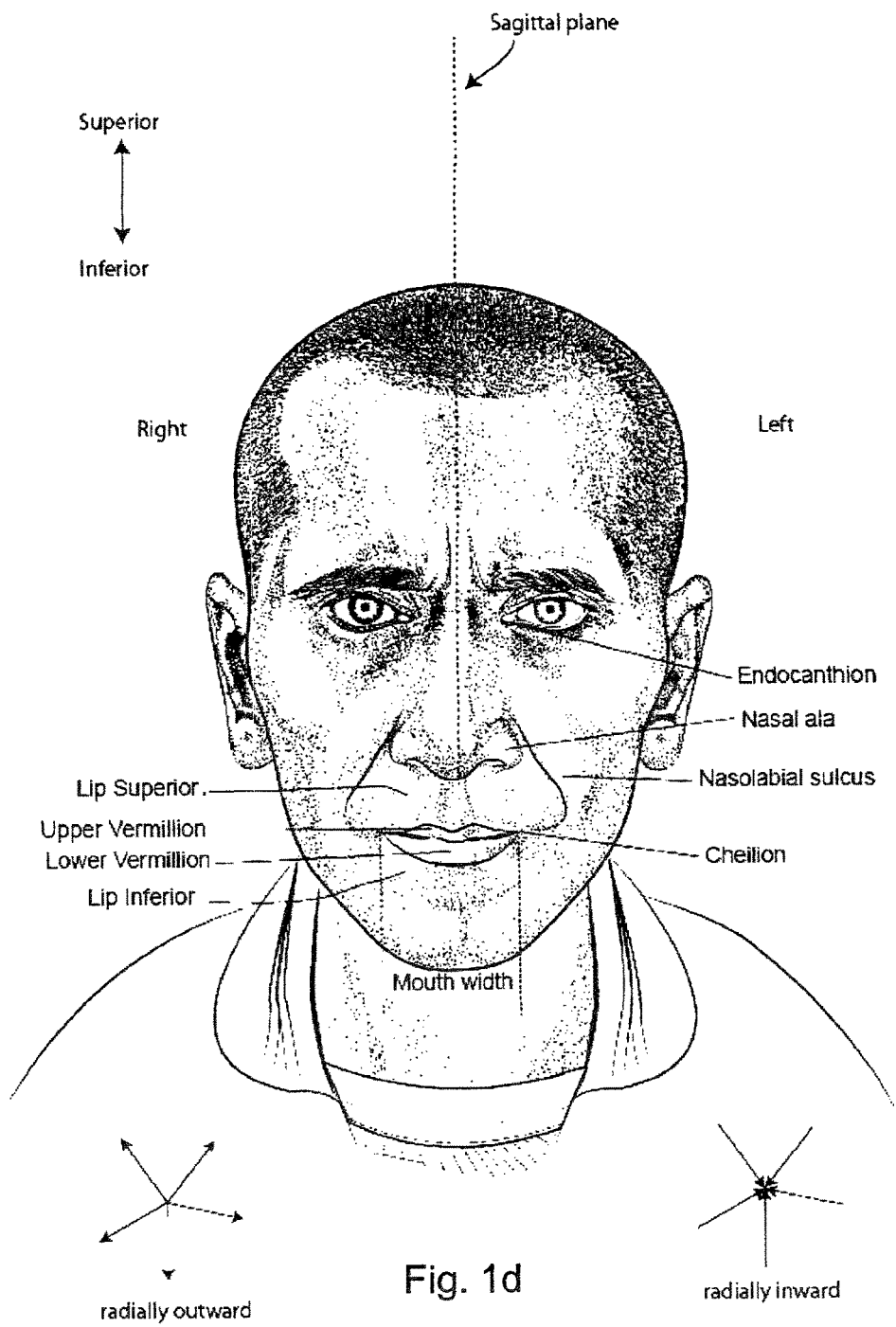
FIG. 1d is a front view of a face with several features of surface anatomy identified including the lip superior, upper vermillion, lower vermillion, lip inferior, mouth width, endocanthion, a nasal ala, nasolabial sulcus and cheilion.
Figure 1E:
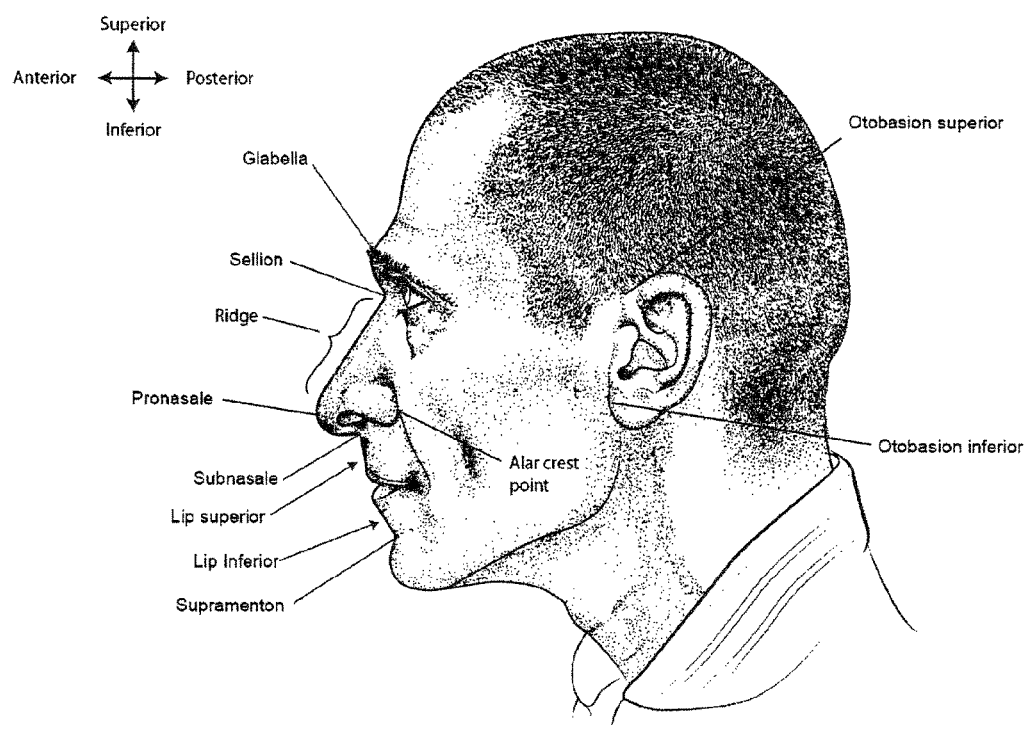
FIG. 1e is a side view of a head with several features of surface anatomy dentified including glabella, sellion, pronasale, subnasale, lip superior, lip inferior, supramenton, nasal ridge, otobasion superior and otobasion inferior. Also indicated are the directions superior & inferior, and anterior & posterior.
Figure 1F:
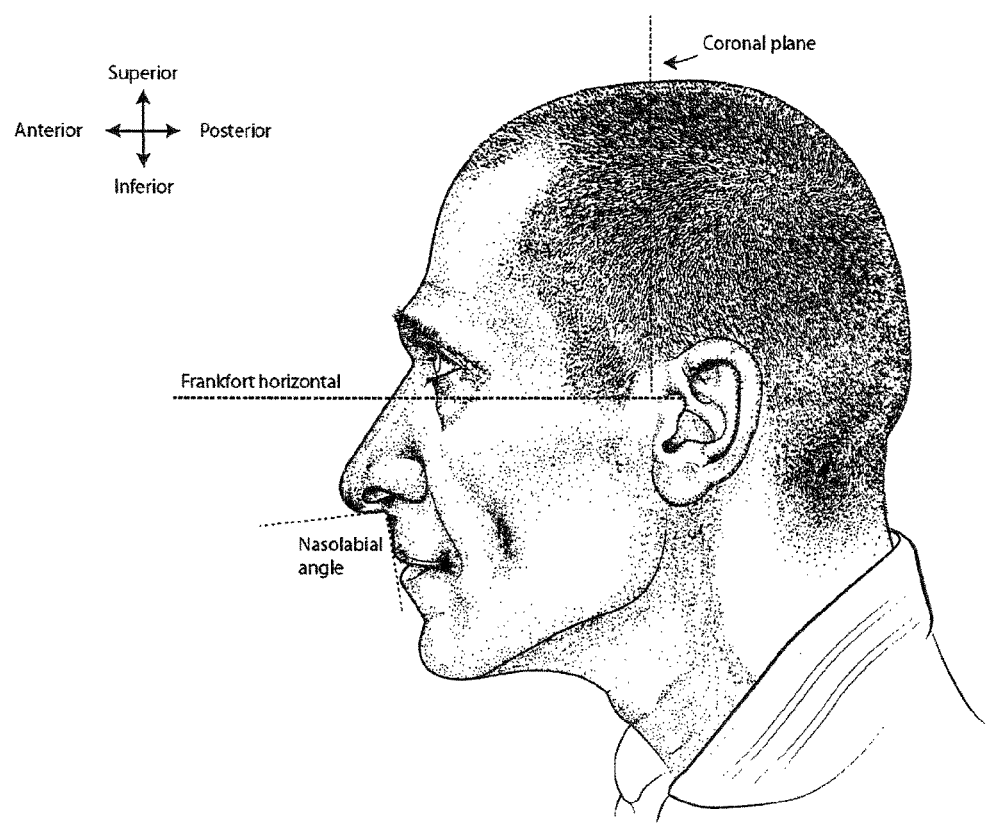
FIG. 1f is a further side view of a head. The approximate locations of the Frankfort horizontal and nasolabial angle are indicated.
Figure 1G:
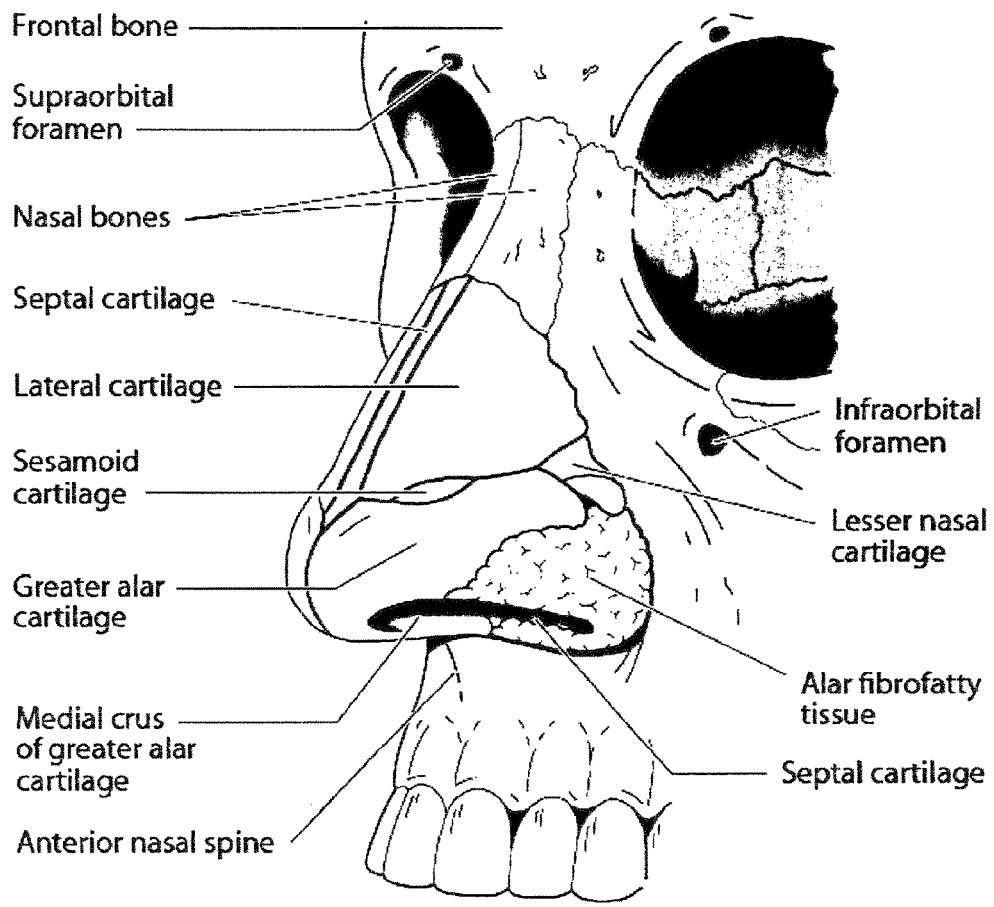
FIG. 1g shows an anterolateral view of a nose

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170 (FIG. 1b, 3, 4). A functional aspect may be provided by one or more physical components. One physical component may provide one or more functional aspects. In use the seal-forming structure 3100 may be arranged to surround an entrance to the airways of the patient so as to facilitate the supply of air at positive pressure to the airways.

Seal-Forming Structure 3100

A seal-forming structure 3100 may provide a sealing-forming portion 11, preferably provided on a pad 10, and a cushion 20. The cushion may at least partially provide a cushioning function.

A seal-forming structure 3100 in accordance with the present technology may be constructed from a soft, flexible, resilient material such as silicone.

The seal-forming structure 3100, preferably the cushion 20, may comprise in a portion of the cushion a sealing flange and a support flange. Preferably the sealing flange comprises a relatively thin member with a thickness of, e.g., less than about 1 mm, for example about 0.25 mm to about 0.45 mm, that extends around the perimeter 3210 of the plenum chamber 3200. The support flange may be relatively thicker than the sealing flange. The support flange may be disposed between the sealing flange and the marginal edge of the plenum chamber 3200, and may extend at least part of the way around the perimeter 3210. The support flange preferably is or includes a spring-like element and functions to support the sealing flange from buckling in use. In use the sealing flange may readily respond to system pressure in the plenum chamber 3200 acting on its underside to urge it into tight sealing engagement with the face.

The seal-forming portion of the non-invasive patient interface 3000 may comprise a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

The non-invasive patient interface 3000 may comprise a seal-forming portion that forms a seal in use on an upper lip region (that is, the lip superior) of the patient's face.

The non-invasive patient interface 3000 may comprise a seal-forming portion that forms a seal in use on a chin-region of the patient's face.

Seal Forming Portion 11

FIG. 2 discloses three seal forming portions 11 in accordance with preferred alternative or combined technologies of the disclosed technology. The seal forming portions may be manufactured using one of the disclosed methods. Left seal forming portion 11 comprises fibers 112 extending from the surface of resilient material 114. Fibers 112 are fixed to surface 112 with an adhesive 113. Fibers 112 form an angle α with the base surface of approximately 90°. Often, the fibers 112 will be randomly distributed. The second seal forming portion located in the middle of FIG. 2 comprises fibers 112' arranged in a plurality of tufts. The tufts are looped at the second free end adapted to get in contact with a patient. The looped distal ends provide an increased wearing comfort. The right sealing portion 11 in FIG. 2 is provided with fibers 112" in a multilevel configuration, i.e. with fibers generally having two or more different, preferably predefined, lengths $l_{112a}$, $l_{112b}$. Although seal forming portion 11 is depicted in the Figures in conjunction with the particularly advantageous cushion 20 and pad 10, seal forming portions 11 may also be used with other pads and/or other cushions.

Pad 10

FIGS. 3 to 8 and 10 to 11 show pad 10 arranged on cushion 20 of patient interface 3000. The pad may be manufactured using one of the disclosed methods. As best seen in FIGS. 3, 4, 7a, 7b, 10 and 11, pad 10 extends along the entire perimeter 3210 of the plenum chamber, i.e. the perimeter of the entrance to the airways of the patient. Pad 10 is generally flat. That is, the width $w_{10}$ of the pad is significantly greater than its thickness $t_{10}$. The front or face contacting surface 11 is contacting the user and forms the seal against the user's face. Although not shown in FIGS. 3 to 7b, face contacting surface 11 preferably comprises the above described seal forming portion 11 with fibers 112. The back surface of pad 10 is adapted to contact cushion 20 in cushion contacting portion 13. The lateral side surfaces at lateral sides 101, 102 may be generally round.

FIG. 12 depicts further preferred shapes of pad 10. Details C and E depict rounded lateral sides 101, 102 whereas the sides of details D and F are generally flat. Overall, details D and F have a flat and rather rectangular of trapezoid shape. The shape may be influenced by the manufacturing process.

FIG. 12 shows on the top left a cross sectional three dimensional view of a pad 10 according to the present technology wherein right below an enlarged detail C of said pad is shown. Similarly, the pads shown on the top right, bottom left and bottom right of FIG. 12 show preferred cushions according to the present technology with respective enlarged details of a cross sectional section thereof. As will be readily noted, the outer circumferential side surface 102 of the cushion may be substantially flat, as, e.g., shown in the top right example, or curved, as shown, e.g., in the top left example. The same applies to the inner circumferential side surface 101 as shown in the examples on the top left and right of FIG. 12. The example on the bottom left shows a rounded outer circumferential surface 102 in combination with a straight inner circumferential surface 101 having a radius, preferably corresponding to about ⅛ to ½ of the pad thickness, at the transition to the seal forming portion or surface 11. This may ease the comfort of the pad when worn by a user. While the pads on the top left and right as well as the bottom left show a substantially flat or planar, eventually slightly concave seal forming portion 11, the pad depicted at the bottom right (see detail F) is exhibits a convexly curved cross-sectional profile.

FIGS. 8a, 8ab are cross sectional views as indicated in FIG. 9b, i.e. views perpendicular to the circumferential direction 3210. As best seen in FIG. 8a, 8b, pad 10 may have different cross-sectional shapes. E.g., cushion contacting portion 13 may be configured to be generally flat while face contacting portion 11 may have a profiled shape. Face contacting portion 11 may have a first concave cross sectional portion followed by a convex peak cross sectional portion and a second concave cross section portion (FIG. 8a and detail F in FIG. 12). Alternatively or additionally, the cross sectional shape may be configured as a convex shape with a gradually reduced gradient towards the outer section of pad 10 as shown in FIG. 8b. Any suitable 2.5D configuration may be applied.

As shown in FIG. 9a, flange portion 26 may be provided with a slit 15 reducing the stiffness of flange portion 26. Portions adjacent to slit 15 at apex P of flange portion 26 depicted in FIG. 9a and located in the nose receiving portion may easier move relative to each other. Such a configuration may facilitate the clamping (FIGS. 5, 7a, 7b). As shown in FIG. 9b, pad 10 may be provided with a corresponding notch or pad slit 15, too.

The pad is provided with a high resilience and is configured to micro-adapt to the patient's face and/or to follow the movements of cushion 20, e.g. pivoting movements of flange 26 depicted in FIG. 5, 7a, 7b. Preferably, as discussed below, the pivoting movements of flange 26 together with other suitable deformations of the cushion achieve a macro-adaptation to the contour and physiognomy of a patients face while the pad provides for a micro-adaptation to said face to enhance, e.g., comfort, sealing characteristics and thus compliance.

Although pad 10 is depicted in the Figures in conjunction with the particularly advantageous seal forming portion 11 and cushion 20, pad 10 may also be used with other cushions and/or other seal forming portions.

Cushion 20

FIG. 5 is an enlarged view of the apex region P depicted in FIG. 4. Cushion 20 supports pad 10 which is positioned at flange 26. The depicted mask comprising cushion 20 and pad 10 may be manufactured using one of the disclosed methods. Flange 26 and web 24 together form a T- or I-shaped beam shape or structure 22. The first end A of structure 22 is fixed to shell or frame 30 of patient interface 3000. Here, a generally chevron- or V-shaped flange of shell or frame 30 is connected to first end A of web portion 24, for instance by co-molding. Part of the shell may also be made of the cushion material. I.e. the cushion may continue to the front area of the patient interface forming part of the shell. Shell or frame 30 may be integrally molded with cushion 20 (FIGS. 3 to 7b). As indicated by arrows in FIG. 5, at least a portion of flange 26, preferably the whole flange 26 may pivot or rock around the second end B. Pad 10 is adapted to follow this movement. When a patient first contacts pad 10 at or close to inner or lateral side 101 pad 10 and flange 26 may pivot around second end B and inner side 101 may move generally in direction C. Depending on the individual shape of the patient's face, it may also be the case that it first contacts the pad at or close to the outer side. In this case, pad 10 and flange 26 may pivot around second end B towards the outer side, opposite direction of C. The cushion and pad, due to their resilience and spring features, may be adapted to cope with and tolerate the resulting torsion as adjacent parts bend inwardly or outwardly. This mechanism allows the system to adapt itself to the patient's individual anatomical distinctiveness in a particularly advantageous fashion. Direction C is opposite the application direction during positioning the mask. I.e. at inner side 101 pad 10 generally moves toward the inner part of cushion 20 (meaning toward the plenum chamber 3200). At the same time, portions of first arm 261 move in generally the same direction. Preferably, portions of second 262 arm may move simultaneously in the opposite direction. I.e. generally in the application direction of the patient interface or towards the patient's face as indicated by curved arrows in FIG. 5. The second end B of web 24 is a center around which the two arms 261, 262 of flange 26 may rock. This rocking motion may be suitable to ensure a near-constant application of the required sealing force onto the patient's face over the entire pad surface, while simultaneously avoiding local areas of increased force.

The resilience of cushion 20 is influenced by the configuration of the first and second arms 261, 261. FIGS. 5 and 6 show the configuration in the apex P region of patient interface 3000. The configuration of the T- or I-beam structured rocker may vary around the perimeter of the entrance to the patient's airways. For instance, arm 261 may be configured more pliable and/or longer in a portion of sealing structure 3100 where a high resilience is required whereas arm 261 may be shorter and/or stiffer in a portion of the sealing structure 3100 which may transmit more interface holding forces to a patient's face. The relative position of the rocker center or second end B may also vary around the perimeter aiming to influence the resilience. The second end B may be located more toward to outer side 102 of flange 26 in portions of sealing structure 3100 in which a high resilience is required than in portions of the sealing structure which may transmit more interface holding forces to a patient's face. The location of the second end B on the flange structure may influence the behavior of the rocking motion in such a way that the system will, in specific areas, more readily deflect towards the mask interior or towards the mask exterior. This may be advantageous in that in protruding areas such as, e.g., the nose ridge or chin, the cushion and pad will be able to deflect towards the interior, whereas in flatter areas such as, e.g., the cheeks, the cushion may be more poised to bend outward. This may be advantageous in enabling the structures to adapt to, and to establish a reliable seal at, different physiological sites in the patient's face. The first arm length or width is referred to as $w_{261}$ while the second arm length or width is referred to as $w_{262}$. Here, in the shown cross-section, the second arm width is smaller or shorter than the first arm width. The resilience of patient interface 3000, inter alia, may be influenced by: 1) the profile and the material of the pad 10 (micro-adaption), 2) the shape of the arms 261, 262 and/or of web portion 24 as well as the material of cushion 20, and/or 3) the relative position of web portion 24 to flange 26 (=ratio of arms length). Accordingly, the disclosed technology provides several design parameters to locally adjust the resilience while having a simple basic design of the patient interface. The simple basic design may allow the use of relatively simple manufacturing processes discussed above without compromising on the comfort.

Moreover, no further time consuming and inappropriate adaption of a patient interface to the individual face of a patient on the macro-adaptation level needs to be carried out. Prior art devices provide semi-rigid plastic deformable cushions which are often inappropriately formed by the patient. In addition, such plastic deformable cushions tend to deform easily, for instance after they are unintentional dropped by a user or even during use.

In one embodiment, flange 26 may only comprise a first arm 261 having portions provided with different arm length and/or different arm stiffnesses thereby varying the resilience of the cushion 20 along the perimeter 3210. By varying the length and/or the stiffness of arm 261, a portion of the first arm 261 located in the nose receiving region may be provided with a higher resilience than another region not located in the nose receiving portion.

Web portion 24 may have an elasticity so as to allow together with above rocker function a clamping onto the patient's nose ridge, preferably on the nasal bones, lateral cartilage and/or sepal cartilage (FIGS. 1g, 5, 7a, 7b, 11) thereby improving the seal. Web portion 24 may be adapted to not significantly collapse when the patient contacts inner side 101. Web portion 24 may be adapted to bulge or move, preferably in a direction D, direction D being generally perpendicular to the main axis of extension of web 24. Web portion 24 may be adapted to move center B of the rocking movement of flange 26 more in a lateral direction D than in the direction of extension of web 24. Preferably, the web 24 is shaped to form a bulge or bellows around the entire perimeter (e.g. FIGS. 11). This bellows is most prominent (e.g. having a smaller radius) where a high resilience is required (e.g. at the nose), and least prominent (e.g. having a bigger radius) where a high stiffness is required (e.g. in the cheeks area). The bulge/bellows will allow the cushion to deflect as the pad comes into contact with prominent features such as the nose. The point B moves roughly in the direction of C, causing the pad and flange features to be pulled inwards in a proximal direction, towards the nose ridge of the patient. The combination of these two effects enables the mask to create a seal by transforming the sealing force, which is applied in a ventral-dorsal plane by the headgear, into a force acting onto the sides of the nose in a proximal direction. This lateral movement of the second end B may further facilitate the clamping of cushion 20 and/or pad 10 onto the patient's nose. When patient interface 3000 is positioned on the nose the laterally displaced rocking center B of web 24 may be biased causing a clamping force on lateral sides of the nose. Cushion 20 and/or pad 10 are provided with a portion of reduced stiffness, here configured as a slit 15. Slit 15 may increase the flexibility or resilience of pad 10 / cushion 20 so as to facilitate the movement indicated by the arrows in FIGS. 5, 7a and 7b and described above. As depicted in FIGS. 11a to 11d, the first and/or second flanges may be provided with at least two portions of different materials. For instance, the first arm 261 may comprise two portions 261-1, 261-2 of different materials. The first portion proximate to second end B may be made of a first material whereas the second distal portion 261-2 may be made of the second material. The first material may be less resilient than the second material. The portions of different materials may be provided around the entire perimeter 3210 of the plenum chamber 3200. Preferably, the portions of different materials are located in sensible areas, e.g. proximal to/around the nose bridge. These portions of different materials may constitute or contribute to the zones of reduce stiffness discussed above.

Although cushion 20 is depicted in the Figures in conjunction with the particularly advantageous seal forming portion 11 and pad 10, cushion 20 may also be used with other pads and/or other seal forming portions.

Plenum Chamber 3200

Preferably the plenum chamber 3200 has a perimeter 3210 that is shaped to be complementary to the surface contour of the face of an average person in the region where a seal will form in use . In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Positioning and Stabilising Structure 3300

Preferably the seal-forming portion 3100 of the patient interface 3000 of the present technology is held in sealing position in use by the positioning and stabilising structure 3300 such as a headgear 3300.

Vent 3400

In one form, the patient interface 3000 includes a vent 3400 constructed and arranged to allow for the washout of exhaled carbon dioxide. One form of vent in accordance with the present technology comprises a plurality of holes, for example, about 20 to about 80 holes, or about 40 to about 60 holes, or about 45 to about 55 holes. Preferably the vent is located in the plenum chamber. Alternatively, the vent is located in a decoupling structure, e.g. a swivel.

Decoupling Structure(s)

In one form the patient interface 3000 includes at least one decoupling structure, for example a swivel or a ball and socket.

Connection Port

Connection port allows for connection to the air circuit.

Forehead Support

In one form, the patient interface 3000 includes a forehead support.

Anti-Asphyxia

In one form, the patient interface includes an anti-asphyxia valve.

Ports

In one form of the present technology, a patient interface 3000 includes one or more ports that allow access to the volume within the plenum chamber. In one form this allows a clinician to supply supplemental oxygen. In one form this allows for the direct measurement of a property of gases within the plenum chamber, such as the pressure.

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

Aspects of a Patient Interface

Frame 30: Frame will be taken to mean a mask structure that bears the load of tension between two or more points of connection with a headgear. A mask frame may be a non-airtight load bearing structure in the mask. However, some forms of mask frame may also be air-tight.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell 30: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight. Shell and frame may be configured as one part, either called frame or shell.

Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

Facial Anatomy (Nose) Ridge (nasal): The nasal ridge is the midline prominence of the nose, extending from the Sellion to the Pronasale.

Lateral nasal cartilage: A generally triangular plate of cartilage. Its superior margin is attached to the nasal bone and frontal process of the maxilla, and its inferior margin is connected to the greater alar cartilage.

Nasal bones: The nasal bones are two small oblong bones, varying in size and form in different individuals; they are placed side by side at the middle and upper part of the face, and form, by their junction, the "bridge" of the nose.

Lateral nasal cartilage: A generally triangular plate of cartilage. Its superior margin is attached to the nasal bone and frontal process of the maxilla, and its inferior margin is connected to the greater alar cartilage.

Septal cartilage (nasal): The nasal septal cartilage forms part of the septum and divides the front part of the nasal cavity.

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "essentially radial" shall also cover exactly radial).

REFERENCE LIST 10 pad
11 seal forming portion
13 cushion contacting portion
15 slit; portion of reduced stiffness
20 resilient cushion,
22 first structure, T- or I-beam shaped structure
24 elongate section or web portion
26 end section or flange portion
30 frame member, frame, shell
101, 102 sides
111 base surface
112 fibers
112' fibers arranged in tufts
112" multilevel arrangement
113 adhesive
114 resilient material,
261 first arm
261-1, 261-2; 262-1, 262-2 two portions made of different materials
262 second arm
3000 patient interface
3100 seal-forming structure
3200 plenum chamber
3210 perimeter of the plenum chamber
3220 marginal edge of the plenum chamber
3300 positioning and stabilising structure
3600 connection port
3700 forehead support
4000 PAP device
4170 air circuit
5000 humidifier
α fiber angle
A first end
B second end
C face contacting side
D lateral direction
1112 fiber length
1112a first length
1112b second length
124 web portion length
P apex of the pad
t10 pad thickness
t24 web portion thickness
t261 flange portion thickness
t261 first arm thickness
t262 second arm thickness
w10 pad width
w13 cushion contacting portion width
w26 width of the flange portion
w261 first arm width
w262 second arm width w262

The invention claimed is:

1. A patient interface comprising a seal forming portion for contacting a patient's skin, a pad, and a cushion;
    wherein the pad comprises a resilient foam material layer constituting a base surface of the seal forming portion, wherein the pad is adapted to be connected to the cushion,
    wherein the seal forming portion comprises the base surface and a plurality of fibers fixed to and extending away from said base surface for contacting the patient's skin; and
    wherein the cushion comprises at least along a portion of a circumference a first structure having an elongate section joined with at least one end section oriented substantially perpendicular or at an angle to the elongate section, wherein a first end of the elongate section is connected or connectable to a frame member, and wherein the at least one end section is provided at an opposing second end of the elongate section, wherein the first structure is a T-beam shaped structure, wherein the elongate section is a web portion and the at least one end section is a flange portion, and wherein the pad is connected to the flange portion.

2. The patient interface according to claim 1, wherein the flange portion is connected or connectable with the pad comprising the seal forming portion.

3. The patient interface according to claim 1, wherein at least a portion of the flange portion is adapted to rotate relative to the second end of the web portion.

4. The patient interface according to claim 1, wherein the flange portion comprises two arms extending from the second end of the web portion in a lateral direction.

5. The patient interface according to claim 4, wherein the flange portion is adapted to rock around the second end, the two arms of the flange portion being rocker arms, wherein the flange portion is adapted to rock around the second end when the patient's skin is in contact.

6. The patient interface according to claim 1, wherein the flange portion is adapted to rock around the second end, and wherein the cushion is provided with a resilience in a nose receiving portion of the cushion so as to clamp the cushion on a ridge of the patient's nose.

7. The patient interface according to claim 1, wherein the web portion is adapted to bulge in a lateral direction.

8. The patient interface according to claim 1, wherein the cushion comprises at least one bellows structure and/or pre-shaped bulge.

9. The patient interface according to claim 1, wherein at least one of the plurality of fibers has a length measured from a proximate end to a distal end between about 0.01 and 5.0 mm.

10. The patient interface according to claim 1, wherein the plurality of fibers provide a higher resilience in the nose ridge area than in other areas of the seal forming portion.

11. The patient interface according to claim 1, wherein the plurality of fibers are made from any one from the group consisting of: cotton, wool, viscose, nylon, and cellulose.

12. The patient interface according to claim 1, wherein the pad has a pad thickness between about 1.5 mm to 26 mm.

13. The patient interface according to claim 1, wherein the pad is provided with a higher resilience than the cushion.

14. The patient interface according to claim 1, wherein the pad comprises a portion of reduced stiffness to facilitate relative movement of portions of the pad adjacent the patient's nose region.

\* \* \* \* \*